US007232437B2

(12) United States Patent
Berman et al.

(10) Patent No.: US 7,232,437 B2
(45) Date of Patent: Jun. 19, 2007

(54) ASSESSMENT OF LESION TRANSMURALITY

(75) Inventors: Adam L. Berman, Dallas, TX (US); Gregory G. Brucker, Minneapolis, MN (US); Robert H. Svenson, Holland Patent, NY (US)

(73) Assignee: Medical CV, Inc., Inver Grove Heights, MN (US)

( * ) Notice: Subject to any disclaimer, the term of this patent is extended or adjusted under 35 U.S.C. 154(b) by 2 days.

(21) Appl. No.: 11/133,900

(22) Filed: May 19, 2005

(65) Prior Publication Data
US 2005/0209589 A1    Sep. 22, 2005

Related U.S. Application Data

(63) Continuation-in-part of application No. 11/102,091, filed on Apr. 8, 2005, and a continuation-in-part of application No. 10/975,674, filed on Oct. 28, 2004.

(60) Provisional application No. 60/516,242, filed on Oct. 31, 2003.

(51) Int. Cl.
*A61B 18/14* (2006.01)
(52) U.S. Cl. .......................... 606/34; 606/41; 600/374
(58) Field of Classification Search .................. 606/7, 606/13–16, 32–35, 41–52; 607/88, 89, 101, 607/102, 104, 122; 600/372–374; 128/898
See application file for complete search history.

(56) References Cited

U.S. PATENT DOCUMENTS 4,693,244 A    9/1987    Daikuzono
4,785,815 A    11/1988   Cohen
4,955,267 A    9/1990    Jacobs et al.
4,985,028 A    1/1991    Isner et al.

(Continued)

FOREIGN PATENT DOCUMENTS

EP    1 170 034 A2    1/2002

(Continued)

OTHER PUBLICATIONS

Abela, *Lasers in Cardiovascular Medicine and Surgery: Fundamentals and Techniques*, p. 28 (1990).

(Continued)

*Primary Examiner*—A. Farah
(74) *Attorney, Agent, or Firm*—Merchant & Gould P.C.

(57) ABSTRACT

A method and apparatus for treating a body tissue in situ (e.g., an atrial tissue of a heart to treat) atrial fibrillation include a lesion formation tool is positioned against the heart surface. The lesion formation tool includes a guide member having a tissue-opposing surface for placement against a heart surface. An ablation member is coupled to the guide member to move in a longitudinal path relative to the guide member. The ablation member has an ablation element for directing ablation energy in an emitting direction away from the tissue-opposing surface. The guide member may be flexible to adjust a shape of the guide member for the longitudinal path to approximate the desired ablation path while maintaining the tissue-opposing surface against the heart surface. In one embodiment, the ablation member includes at least one radiation-emitting member disposed to travel in the longitudinal pathway. Transmurality can be assessed to approximate a location of non-transmurality in a formed lesion.

12 Claims, 21 Drawing Sheets

U.S. PATENT DOCUMENTS

| | | | |
|---|---|---|---|
| 4,997,431 A | 3/1991 | Isner et al. | |
| 5,046,810 A | 9/1991 | Steiner et al. | |
| 5,104,393 A | 4/1992 | Isner et al. | |
| 5,125,926 A | 6/1992 | Rudko et al. | |
| 5,172,699 A | 12/1992 | Svenson et al. | |
| 5,281,212 A | 1/1994 | Savage et al. | |
| 5,282,798 A | 2/1994 | Bruse et al. | |
| 5,290,277 A | 3/1994 | Vercimak et al. | |
| 5,306,274 A | 4/1994 | Long | |
| 5,318,525 A | 6/1994 | West et al. | |
| 5,354,296 A | 10/1994 | Turkel | |
| 5,368,564 A | 11/1994 | Savage | |
| 5,380,316 A | 1/1995 | Aita et al. | |
| 5,389,096 A | 2/1995 | Aita et al. | |
| 5,409,008 A | 4/1995 | Svenson et al. | |
| 5,423,805 A | 6/1995 | Brucker et al. | |
| 5,500,012 A | 3/1996 | Brucker et al. | |
| 5,501,271 A | 3/1996 | Wijkstrom | |
| 5,507,725 A | 4/1996 | Savage et al. | |
| 5,534,000 A | 7/1996 | Bruce | |
| 5,537,499 A | 7/1996 | Brekke | |
| 5,728,091 A | 3/1998 | Payne et al. | |
| 5,769,843 A | 6/1998 | Abela et al. | |
| 5,782,828 A | 7/1998 | Chen et al. | |
| 5,800,428 A | 9/1998 | Nelson et al. | |
| 5,824,005 A | 10/1998 | Motamedi et al. | |
| 5,827,267 A | 10/1998 | Savage et al. | |
| 5,830,209 A | 11/1998 | Savage et al. | |
| 5,897,551 A | 4/1999 | Everett et al. | |
| 5,925,033 A | 7/1999 | Aita et al. | |
| 5,951,541 A | 9/1999 | Simpson et al. | |
| 6,024,739 A | 2/2000 | Ponzi et al. | |
| 6,063,080 A | 5/2000 | Nelson et al. | |
| 6,063,081 A | 5/2000 | Mulier et al. | |
| 6,066,131 A | 5/2000 | Mueller et al. | |
| 6,068,629 A | 5/2000 | Haissaguerre et al. | |
| 6,110,167 A | 8/2000 | Cozean et al. | |
| 6,135,996 A | 10/2000 | Kolesa et al. | |
| 6,138,043 A * | 10/2000 | Avitall | 600/377 |
| 6,161,543 A | 12/2000 | Cox et al. | |
| 6,200,308 B1 | 3/2001 | Pope et al. | |
| 6,200,310 B1 | 3/2001 | Ben-Haim et al. | |
| 6,231,518 B1 | 5/2001 | Grabek et al. | |
| 6,231,568 B1 | 5/2001 | Loeb et al. | |
| 6,237,605 B1 * | 5/2001 | Vaska et al. | 128/898 |
| 6,258,083 B1 | 7/2001 | Daniel et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,474,340 B1 | 11/2002 | Vaska et al. | |
| 6,514,244 B2 | 2/2003 | Pope et al. | |
| 6,514,250 B1 * | 2/2003 | Jahns et al. | 606/41 |
| 6,517,536 B2 | 2/2003 | Hooven et al. | |
| 6,527,767 B2 * | 3/2003 | Wang et al. | 606/32 |
| 6,546,935 B2 | 4/2003 | Hooven | |
| 6,558,375 B1 | 5/2003 | Sinofsky et al. | |
| 6,558,382 B2 | 5/2003 | Jahns et al. | |
| 6,572,609 B1 | 6/2003 | Farr et al. | |
| 6,579,285 B2 | 6/2003 | Sinofsky | |
| 6,599,288 B2 | 7/2003 | Maguire et al. | |
| 6,663,622 B1 * | 12/2003 | Foley et al. | 606/34 |
| 6,736,808 B1 | 5/2004 | Motamedi et al. | |
| 6,743,225 B2 | 6/2004 | Sanchez et al. | |
| 6,802,840 B2 | 10/2004 | Chin et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,817,999 B2 | 11/2004 | Berube et al. | |
| 6,899,710 B2 | 5/2005 | Hooven | |
| 6,949,095 B2 | 9/2005 | Vaska et al. | |
| 6,953,457 B2 | 10/2005 | Farr et al. | |
| 6,971,394 B2 | 12/2005 | Sliwa, Jr. et al. | |
| 2002/0052621 A1 | 5/2002 | Fried et al. | |
| 2002/0087151 A1 | 7/2002 | Mody et al. | |
| 2002/0100485 A1 | 8/2002 | Stevens et al. | |
| 2002/0128636 A1 | 9/2002 | Chin et al. | |
| 2003/0023236 A1 | 1/2003 | Gowda et al. | |
| 2003/0029462 A1 | 2/2003 | Cox et al. | |
| 2003/0050630 A1 | 3/2003 | Mody et al. | |
| 2003/0050631 A1 | 3/2003 | Mody et al. | |
| 2003/0069575 A1 | 4/2003 | Chin et al. | |
| 2003/0069577 A1 | 4/2003 | Vaska et al. | |
| 2003/0083654 A1 | 5/2003 | Chin et al. | |
| 2003/0120268 A1 | 6/2003 | Bertolero et al. | |
| 2003/0125730 A1 | 7/2003 | Berube et al. | |
| 2003/0163128 A1 | 8/2003 | Patil et al. | |
| 2003/0195496 A1 | 10/2003 | Maguire et al. | |
| 2003/0199860 A1 | 10/2003 | Loeb et al. | |
| 2003/0220639 A1 | 11/2003 | Chapelon et al. | |
| 2004/0006333 A1 | 1/2004 | Arnold et al. | |
| 2004/0019348 A1 | 1/2004 | Stevens et al. | |
| 2004/0054363 A1 | 3/2004 | Vaska et al. | |
| 2004/0073206 A1 * | 4/2004 | Foley et al. | 606/34 |
| 2004/0102771 A1 | 5/2004 | Bertolero et al. | |
| 2004/0143257 A1 | 7/2004 | Fuimaono | |
| 2004/0147912 A1 | 7/2004 | Sinofsky | |
| 2004/0147913 A1 | 7/2004 | Sinofsky | |
| 2004/0260278 A1 | 12/2004 | Anderson et al. | |
| 2005/0033284 A1 * | 2/2005 | Hooven et al. | 606/41 |
| 2005/0075629 A1 | 4/2005 | Chapelon et al. | |
| 2005/0090815 A1 * | 4/2005 | Francischelli et al. | 606/32 |
| 2005/0096643 A1 | 5/2005 | Brucker et al. | |
| 2005/0171521 A1 * | 8/2005 | Brucker et al. | 606/15 |
| 2005/0182392 A1 | 8/2005 | Brucker et al. | |
| 2005/0209589 A1 | 9/2005 | Berman et al. | |
| 2005/0273090 A1 | 12/2005 | Nieman et al. | |
| 2006/0009759 A1 | 1/2006 | Christian et al. | |
| 2006/0025762 A1 | 2/2006 | Mohan et al. | |
| 2006/0084960 A1 | 4/2006 | Mester et al. | |

FOREIGN PATENT DOCUMENTS

| | | |
|---|---|---|
| WO | WO 01/58373 A1 | 8/2001 |
| WO | WO 2006/050011 A1 | 5/2006 |

OTHER PUBLICATIONS

Chiappini, et al., "Cox/Maze III Operation Versus Radiofrequency Ablation for the Surgical Treatment of Atrial Fibrillation: A Comparative Study," *Ann. Thorac. Surg.*, No. 77, pp. 87-92 (2004).

Cox, "Atrial fibrillation II: Rationale for surgical treatment," *The Journal of Thoracic and Cardiovascular Surgery*, vol. 126, No. 6, pp. 1693-1699 (2003).

Fried, N. et al., "Linear Lesions in Myocardium Created by Nd:YAG Laser Using Diffusing Optical Fibers: In Vitro and In Vivo Results," *Lasers in Surgery and Medicine*, vol. 27, pp. 295-304 (2000).

Fuller, I. et al., "Intramural Coronary Vasculature Prevents Transmural Radiofrequency Lesion Formation. Implications for Linear Ablation," *Circulation*, vol. 107, pp. 1797-1803 (Apr. 2003).

Keane, D. et al., "Linear Atrial Ablation With a Diode Laser and Fiberoptic Catheter," *Circulation*, vol. 100, e59-e60 (1999).

Kubota, H. et al., "Atrial Ablation With an IRK-151 Infrared Coagulator," *Ann. Thorac. Surg.*, vol. 66, pp. 95-100 (1998).

Thomas, S. et al., Production of Narrow but Deep Lesions Suitable for Ablation of Atrial Fibrillation Using a Saline-Cooled Narrow Beam Nd:YAG Laser Catheter, *Lasers in Surgery and Medicine*, vol. 38, pp. 375-380 (2001).

van Brakel, T. et al., "Evaluation of Epicardial Microwave Ablation Lesions: Histology Versus Electrophysiology," *Ann. Thorac. Surg.*, vol. 78, pp. 1397-1402 (2004).

"Vascu-Statt® Single-Use Bulldog Clamps," Scanlan International, http://www.scanlaninternational.com/singleuse/vascustatt.asp, 1 page (Copyright 2004).

Viola et al., "The Technology in Use for the Surgical Ablation of Atrial Fibrillation," *Seminars in Thoracic and Cardiovascular Surgery*, vol. 14, No. 3, pp. 198-205 (2002).

Ware, D. et al., "Slow Intramural Heating With Diffused Laser Light: A Unique Method for Deep Myocardial Coagulation," *Circulation*, vol. 99, pp. 1630-1636 (Mar. 30, 1999).

Bruneval, P. et al., "Nd-YAG laser-induced injury in dog myocardium: optical and ultrastructural study of early lesions," *European Heart Journal*, vol. 8, pp. 785-792 (1987).

Curtis, A. et al., "Modification of Atrioventricular Conduction Using a Combined Laser-Electrode Catheter," *PACE*, vol. 17, Part 1, pp. 337-348 (Mar. 1994).

Derbyshire, G. et al., "Thermally Induced Optical Property Changes in Myocardium at 1.06 μm," *Lasers in Surgery and Medicine*, vol. 10, pp. 28-34 (1990).

Hindricks, G. et al., "Precutaneous endocardial application of Nd-YAG laser energy: an experimental feasibility study for ablation of ventricular myocardium," *Z. Kardiol*, vol. 80, pp. 673-680 (1991) (Summary in English).

Hirao, K. et al., "Transcatheter Neodymium-Yttrium-Aluminum-Garnet Laser Coagulation of Canine Ventricle Using a Balloon-Tipped Cardioscope," *Japanese Circulation Journal*, vol. 61, pp. 695-703 (Aug. 1997).

Inoue, Y. et al., "Feasibility Study of Vascular-Endoscopic Valvuloplasty. Using a Laser and Flexible Endoscope," *ASAIO Journal*, vol. 40, pp. M811-M815 (1994).

Ischinger, T. et al., "The use of thermal laser action for cardiovascular recanalization; an example of Nd:YAG laser," *Z. Kardiol*, vol. 8, pp. 689-700 (1989) (Summary in English).

Littmann, L. et al., "Catherization Technique for Laser Photoablation of Atrioventricular Conduction from the Aortic Root in Dogs," *PACE*, vol. 16, Part 1, pp. 401-406 (Mar. 1993).

Littmann, L. et al., "Neodymium:YAG Contact Laser Photocoagulation of the In Vivo Canine Epicardium: Dosimetry, Effects of Various Lasing Modes, and Histology," *Lasers in Surgery and Medicine*, vol. 13, pp. 158-167 (1993).

Menz, V. et al., "Linear Lesion Formation by ND:YAG Laser Versus Radiofrequency Energy in Porcine Atria," *PACE*, vol. 23, Part II, pp. 1848-1851 (Nov. 2000).

Obelienius, V. et al., "Histological Studies of Myocardium Zones Irradiated with Nd-YAG Laser," *Lasers in Surgery and Medicine*, vol. 5, pp. 475-483 (1985), vol. 5, pp. 475-483 (1985).

Obelienius, V. et al., "Transvenous Ablation of the Atrioventricular Conduction System by Laser Irradiation Under Endoscopic Control," *Lasers in Surgery and Medicine*, vol. 5, pp. 469-474 (1985).

Ogura, M. et al., "Myocardium Tissue Ablation with High-Peak-Power Nanosecond 1,064- and 532-nm Pulsed Lasers: Influence of Laser-Induced Plasma," *Lasers in Surgery and Medicine*, vol. 31, pp. 136-141 (2002).

Ohtake, H. et al., "Myocardial Coagulation by Intraoperative Nd:YAG Laser Ablation and its Dependence on Blood Perfusion," *PACE*, vol. 17, pp. 1627-1631 (Oct. 1994).

Ohtake, H. et al., "A New Contact Probe for Intraoperative Laser Ablation," *PACE*, vol. 19, Part I, pp. 2060-2065 (Dec. 1996).

Schuger, C. et al., "Precutaneous Transcatheter Laser Balloon Ablation from the Canine Coronary Sinus: Implications for the Wolff-Parkinson-White Syndrome," *Lasers in Surgery and Medicine*, vol. 10, 140-148 (1990).

Selle, J. et al., "Successful Clinical Laser Ablation of Ventricular Tachycardia: A Promising New Therapeutic Method," *Ann. Thorac. Surg.*, vol. 42, No. 4, pp. 380-384 (Oct. 1986).

Selle, J. et al., "Laser Ablation of Ventricular Tachycardia," *Thorac. Cardiovasc. Surgeon*, vol. 36, pp. 155-158 (Special Issue) (1988).

Splinter, R. et al., "Optical Properties of Normal, Diseased, and Laser Photocoagualted Myocardium at the Nd:YAG Wavelength," *Lasers in Surgery and Medicine*, vol. 11, pp. 117-124 (1991).

Splinter, R. et al., "Ultrasonic Characterization of Myocardial Photocoagulation Lesion Size in Vivo During Nd:YAG Laser Irradiation," *J. Clin. Ultrasound*, vol. 22, No. 4, pp. 221-229 (May 1994).

Svenson, R. et al., "Neodymium: YAG laser photocoagulation: a successful new map-guided technique for the intraoperative ablation of ventricular tachycardia," *Circulation*, vol. 76, No. 6, pp. 1319-1328 (Dec. 1987).

Svenson et al., "Regional Atrial Electrical Isolation. Lines of Block Created By Laser Photocoagulation: A Possible Intraoperative Approach To Atrial Fibrillation", *PACE*, vol. 22, p. 774 (Abstract) (Apr. 1999).

Verdaasdonk, R. et al., "Explosive onset of continuous wave laser tissue ablation," *Phys. Med. Biol.*, vol. 35, No. 8, pp. 1129-1144 (1990).

Wagshall, et al., "A Novel Catheter Design For Laser Photocoagulation Of The Myocardium To Ablate Ventricular Tachycardia", *Journal of Interventional Cardiac Electrophysiology*, Aug.;7(1), pp. 13-22 (2002).

Weber, H. et al., "Precutaneous Nd:YAG Laser Coagulation of Ventricular Myocardium in Dogs Using a Special Electrode Laser Catheter," *PACE*, vol. 12, pp. 899-910 (Jun. 1989).

Weber, H. et al., "Effects of Nd:YAG Laser Coagulation of Myocardium on Coronary Vessels," *Lasers in Surgery and Medicine*, vol. 10, pp. 133-139 (1990).

Weber, H. et al., "Catheter-directed laser coagulation of atrial myocardium in dogs," *European Heart Journal*, vol. 15, pp. 971-980 (1994).

Weber, H. et al., "Laser catheter ablation of atrial flutter and of atrioventricular nodal reentrant tachycardia in a single session," *European Heart Journal*, vol. 15, pp. 1147-1149 (1994).

Weber, H. et al., "Mapping Guided Laser Catheter Ablation of the Atrioventricular Conduction in Dogs," *PACE*, vol. 19, pp. 176-187 (Feb. 1996).

Weber, H. et al., "Laser catheter coagulation of atrial mycoardium for ablation of atrioventricular nodal reentrant tachycardia. First clinical experience," *European Heart Journal*, vol. 18, pp. 487-495 (1997).

Weber, H. et al., "Laser versus Radiofrequency Catheter Ablation of Ventricular Myocardium in Dogs: A Comparative Test," *Cardiology*, vol. 88, pp. 346-352 (1997).

Weber, H. et al., "Laser Catheter Coagulation of Normal and Scarred Ventricular Myocardium in Dogs." *Lasers in Surgery and Medicine*, vol. 22, pp. 109-119 (1998).

Wietholt, D. et al., "Nd:YAG Laser-Photocoagulation: Acute Electrophysiological, Hemodynamic, and Morphological Effects in Large Irradiated Areas," *PACE*, vol. 15, pp. 52-59 (Jan. 1992).

\* cited by examiner

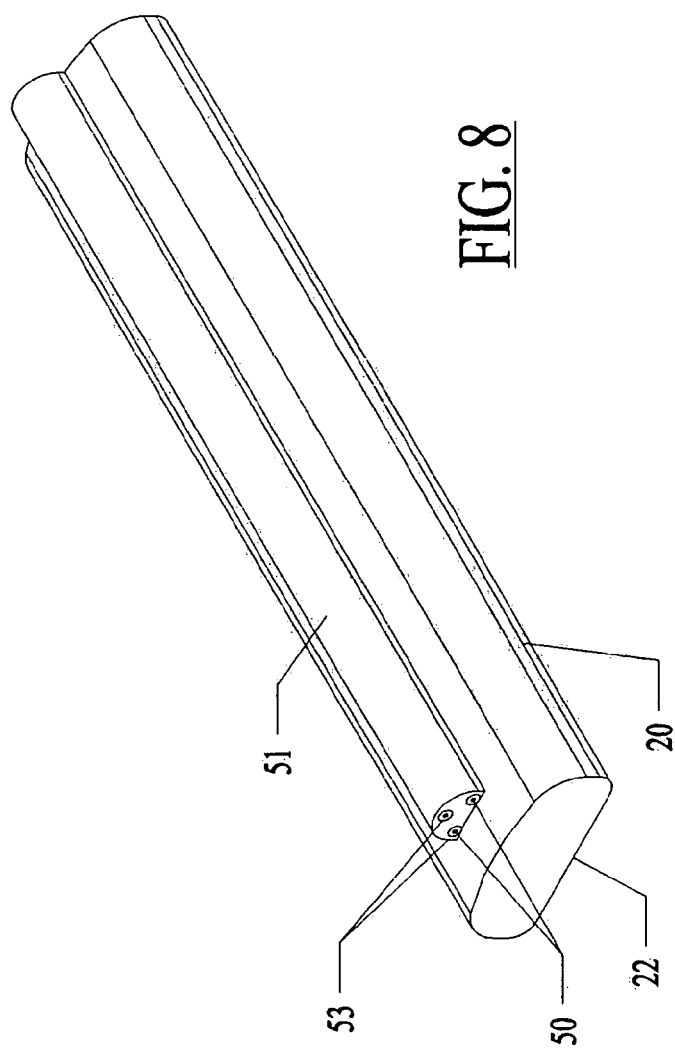
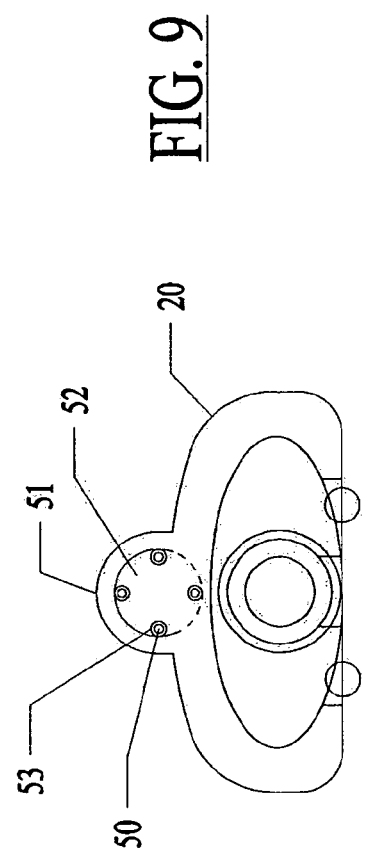
FIG. 8
FIG. 9

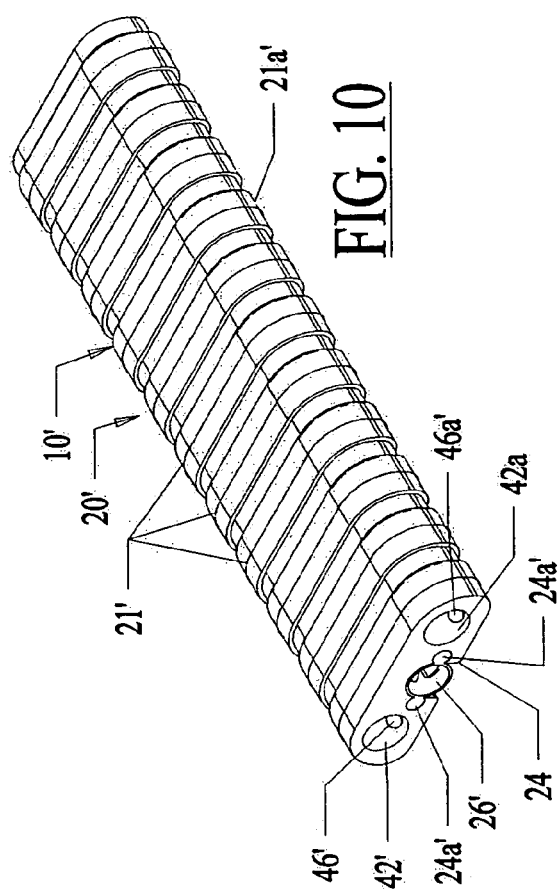
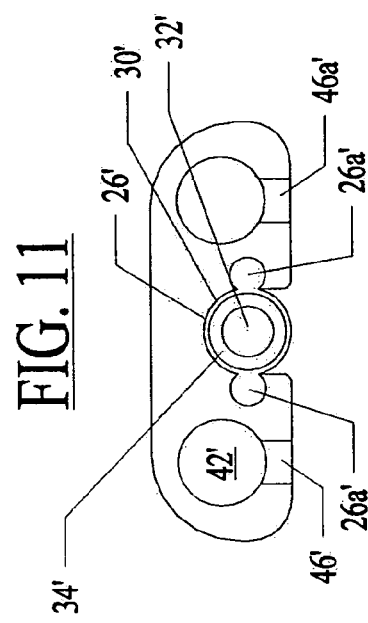
FIG. 10
FIG. 11

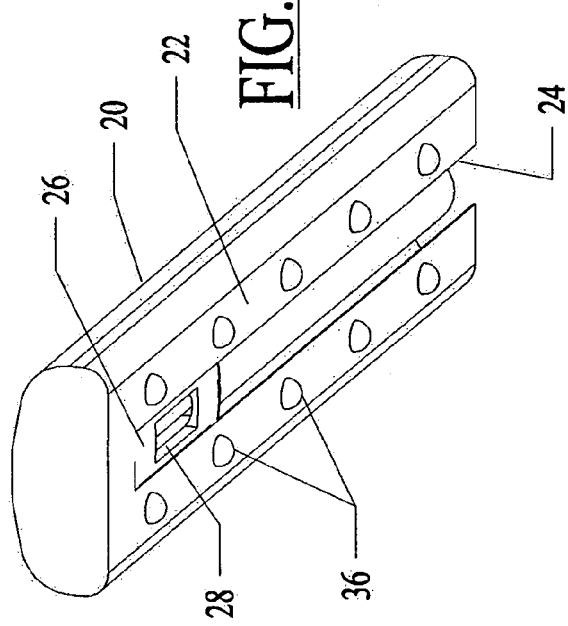
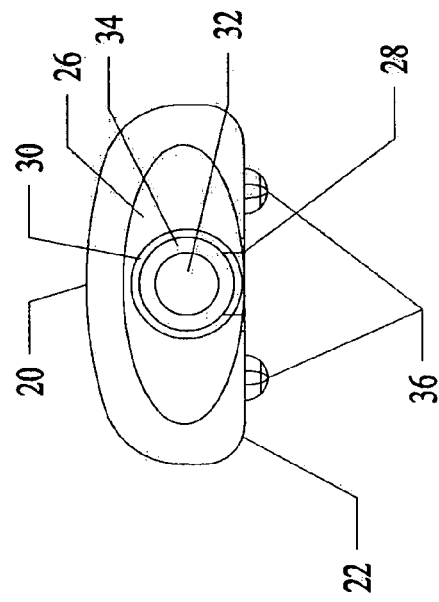

ASSESSMENT OF LESION TRANSMURALITY

CROSS-REFERENCE TO RELATED APPLICATION

This patent application is continuation-in-part of commonly assigned U.S. patent application Ser. No. 11/102,091 filed in the names of co-inventors Gregory G. Brucker, Adam L. Berman, Damian A. Jelich, Dana R. Mester and Robert W. Clapp on Apr. 8, 2005 and entitled "Apparatus and Method for Guided Ablation Treatment" and filed as a continuation-in-part application of U.S. patent application Ser. No. 10/975,674 filed Oct. 28, 2004 titled "Apparatus and Method for Laser Treatment" and which claims priority to U.S. Provisional Patent Application Ser. No. 60/516,242 with an assigned filing date of Oct. 31, 2003. The present application claims priority to all of the foregoing.

BACKGROUND OF THE INVENTION

1. Field of the Invention

The present invention relates to surgical instruments for laser cardiac ablation procedures. More particularly, the invention relates to an ablation apparatus with a guide member to guide the ablation apparatus in a desired pattern.

2. Description of the Prior Art

A. Atrial Fibrillation

It is known that at least some forms of cardiac arrhythmia are caused by electrical impulses traveling through the cardiac muscle tissue by abnormal routes. In a normal, non-arrhythmic heart, electrical nerve impulses travel in an orderly and well-defined fashion through the sinoatrial node and then through the atrioventricular node in order to create an orderly flow of electrical impulses that lead to contraction in the heart.

In cardiac arrhythmias, cardiac impulses travel along undesirable pathways through the cardiac tissue leading to a rapid heart beat (tachycardia), slow heart beat (bradycardia) or a disorderly heart beat (fibrillation). Atrial fibrillation (AF) is a chaotic heart rhythm of the atrial chambers of the heart. Atrial fibrillation prevents the heart from pumping blood efficiently causing reduced physical activity, stroke, congestive heart failure, cardiomyopathy and death.

B. Maze Procedure—Generally

One technique for treating atrial fibrillation is to surgically create lines in the heart muscle tissue (myocardium) whereby electrical conduction of nerve impulses is blocked or rerouted. This technique for creating lines of electrical blockage is referred to as the Maze procedure.

Initial approaches to performing the Maze procedure involved invasive surgery in which a series of linear incisions are made in the cardiac tissue and then sutured together. The lines of scar tissue that form in the incisions do not conduct electrical impulses and are intended to prevent disorderly contraction of the atrial tissue.

In a typical Maze procedure, up to six non-conductive lines are required. Each of the non-conductive lines is typically several centimeters in length. Once these lines scar and heal, they disrupt electrical pathways that may cause atrial fibrillation. Examples of the Maze procedure and other surgical techniques for treating atrial fibrillation are described in Chiappini, et al., "Cox/Maze III Operation Versus Radiofrequency Ablation for the Surgical Treatment of Atrial Fibrillation: A Comparison Study", *Ann. Thorac. Surg.*, No. 77, pp. 87-92 (2004) and Cox, "Atrial fibrillation II: Rationale for surgical treatment", *J. Thoracic and Cardiovascular Surg.*, Vol. 126, No. 6, pp. 1693-1699 (2003).

C. Less Invasive Maze Procedure Technologies

Less invasive ablation techniques have also been utilized to perform the Maze procedure. In such techniques, the surgeon typically drags an a radiofrequency (RF) electrode in a linear fashion along the endocardial (internal) or epicardial (external) surface of the heart to produce a series of lesions using heat to desiccated and ultimately kill cardiac cells. The scaring created by the lesions is ideally contiguous and non-conductive of electrical impulses. For endocardial use, standard ablation catheters or catheters with extended distal electrodes are employed. Epicardially, specially designed handheld probes with a distal electrode for the application of ablating energy are often used.

For the greatest likelihood of success in a Maze procedure, it is particularly important that the lesions created be transmural. A transmural lesion extends through the full wall thickness of the cardiac muscle at the location of the lesion. One factor that limits transmurality of lesions from the epicardium is the cooling effect of blood in and around the heart particularly during 'off-pump' procedures during which the heart is beating. This is particularly difficult when radio frequency (RF) energy is employed because it relies exclusively on thermal diffusion to create transmural lesions i.e, flow of heat from higher to lower temperature. The cooling effect of blood on the endocardial surface within the atrium limits attainment of the temperature required to form thermal lesions.

The maximum temperature, at electrode/tissue interface, is also limited to something less than the boiling point of water. Higher temperatures cause boiling of interstitial water creating explosions and subsequent tissue perforations. Perforations of the atrial wall leads to a weakening of the heart structure as well as significant bleeding during surgery that must be controlled.

Additionally, high electrode/tissue temperatures can create burns and adhesion between the probe and the heart tissue. Such adhesions can insulate the probe from the heart tissue blocking the efficient application of energy. These procedures are also a problem for the surgeon and staff who often must stop to clean the tip of the probe.

The efficacy of creating transmural lesions with RF can be enhanced by using a second electrode at the endocardial surface. The endocardial electrode provides a more direct electrical path through cardiac tissue which 'focuses' the energy more directly at the target site and secondarily protects the endocardial surface from direct cooling by blood flow in the left atrium. This approach requires access into the left atrium which adds complexity and increases risk to the patient.

The same analysis can also be applied to cryogenic methods which freeze interstitial water causing cellular death. However in this application, the blood warms the tissue at the endocardial surface which again limits the attainment of temperatures required to cause cellular death and create transmural lesions.

A discussion of techniques and technologies for treating atrial fibrillation is set forth in Viola, et al., "The Technology in Use for the Surgical Ablation of Atrial Fibrillation", *Seminars in Thoracic and Cardiovascular Surgery*, Vol. 14, No. 3, pp. 198-205 (2002). Viola et al. describe numerous ablation technologies for treating atrial fibrillation with the Maze procedure. These include cryosurgery, microwave energy, radiofrequency energy, and laser ablation.

D. Laser Ablation and the Maze Procedure

The use of lasers in treating atrial fibrillation is desirable because laser energy is first and foremost light which is subsequently converted to heat. Thus, the principles for transmission of light can be used to 'diffuse' laser energy in cardiac tissue. At selected wavelengths, light diffusion can be significantly faster and penetrate more deeply than thermal diffusion. To achieve this effect, it is important to understand the spectral characteristics of atrial tissue and select a laser wavelength with high transmissivity, i.e., low absorption. Wavelengths in the near infrared region, 700-1200 nanometers are suitable for achieving such results. Ideally the wavelength would be 790 to 830 or 1020 to 1140 nanometers. As a result, laser ablation is fast and results in narrow lesions. Viola, et al., "The Technology in Use for the Surgical Ablation of Atrial Fibrillation", *Seminars in Thoracic and Cardiovascular Surgery*, Vol. 14, No. 3, pp. 201, 204 (2002). However, in the prior art, laser ablation for treating atrial fibrillation has been troublesome.

Viola et al. discuss problems associated with the use of laser energy to treat atrial fibrillation. These concerns are directed to safety and reliability and note that lasers are prone to overheating because of the absence of a self-limiting mechanism. The authors note that over-heating with lasers can lead to crater formation and eventually to perforation, especially when using pin-tip devices. Viola, et al., supra, at p. 203. The authors note that the high power of laser ablation (described as 30 to 80 Watts) results in the laser technique not being widely clinically applied. Id., at p. 201. The mechanical effects resulting from direct heating of the myocardial tissue with laser energy results in cellular explosions caused by shock waves. Viola, et al., supra, at p. 201.

The possibility for perforation of the myocardium with laser energy raises a particular concern for treating atrial fibrillation. The myocardial wall of the atria is quite thin (e.g., about 2 mm in thickness in some locations). A coring of the myocardium by a laser could result in a full wall thickness perforation and resulting leakage of blood.

Viola et al. note the development of a long probe laser that allows diffusion of the laser thermal energy over the long probe tip in a unidirectional fashion. Id., at p. 201. While not mentioning the source of this long probe tip, it is believed by the present inventors to be referring to the atrial fibrillation laser of CardioFocus, Inc., Norton, Mass. (USA) as described in U.S. Patent Application Publication No. 2004/6333A1 in the name of Arnold, et al. (published Jan. 8, 2004) and U.S. Pat. No. 6,579,285 issued to Sinosky. This technology as practiced differs in two ways to that of the present invention. First, and most importantly, it defocuses the coherent laser beam by using reflective particles to scatter the light longitudinally and radially before it enters the tissue. This reduces the longitudinal movement required to produce linear lesions but, by decreasing the coherency of the laser beam before entering cardiac tissue, and negates many of the advantages of light to more deeply penetrate cardiac tissue. Secondly, this technology uses laser light in the 910 to 980 nanometer wavelengths which has a significant water absorption peak compared to 810 and 1064. The higher absorption reduces the penetration of the laser light through cardiac tissue. Reducing energy penetration depths increases the risk (particularly on a beating heart) of creating a lesion that is less than transmural.

E. Conductivity Verification

A further difficulty with creating linear nonconductive lesions is the inability to verify that a truly nonconductive lesion has been produced. If a transmural lesion is not properly formed in accordance with the Maze procedure, the treatment for atrial fibrillation may not be successful. This could require a second surgical procedure. It would be helpful if the surgeon could promptly discern whether a particular linear lesion is truly non-conducting at the time of the original procedure to permit correction at that time. This would enable prompt re-treatment if necessary.

F. Placing and Guiding an Atrial Ablation Tool

The afore-mentioned U.S. patent application Ser. No. 10/975,674 describes formation of a lesion pattern by a surgeon moving the tip of a wand over the heart surface. Use of a tool to guide or control an ablation tool has been suggested. For example, U.S. Pat. No. 6,579,285 (assigned to CardioFocus, Inc.) shows a diffused light fiber tip in a malleable housing. The housing is bent to form a desired shape and placed against the heart. The diffused light fiber tip is moved through the housing in a series of steps to form a lesion. The lesion is formed by stopping the fiber at a location, energizing the motionless fiber to create a lesion, and moving the fiber to a new location to form a subsequent lesion segment. A similar arrangement for an ablation tool is shown in U.S. patent publication No. 2002/0087151 published Jul. 4, 2002 (assigned to AFx, Inc.).

U.S. patent publication No. 2004/0102771 published May 27, 2004 (assigned to Estech, Inc.) describes a device to guide an ablation tool while maintaining contact between the heart and an ablation device. Other devices for either guiding an ablation element or for maintaining contact for between an ablation element and the heart are shown in U.S. Pat. No. 6,237,605 (assigned to Epicor, Inc.). The '605 patent describes using vacuum against an epicardium or an inflatable balloon against a pericardium to maintain ablation devices in a fixed position against the heart. U.S. Pat. Nos. 6,514,250 and 6,558,382 (both assigned to Medtronic, Inc.) describe suction to hold ablation elements against a heart.

SUMMARY OF THE INVENTION

According to a preferred embodiment of the present invention, a method and apparatus are disclosed for treating a body tissue in situ (e.g., atrial tissue of a heart to treat) atrial fibrillation. The method and apparatus include identifying a patient with atrial fibrillation and accessing a surface of the tissue. A lesion formation tool is positioned against the accessed surface. The lesion formation tool includes a guide member having a tissue-opposing surface for placement against a heart surface. An ablation member is coupled to the guide member to move in a longitudinal path relative to the guide member. The ablation member has an ablation element for directing ablation energy in an emitting direction away from the tissue-opposing surface. In a preferred embodiment, the guide member is flexible to adjust a shape of the guide member for the longitudinal path to approximate the desired ablation path while maintaining the tissue-opposing surface against the heart surface. In one embodiment, the ablation member includes at least one radiation-emitting member disposed to travel in the longitudinal pathway. In another embodiment, the guide member has a plurality of longitudinally spaced apart tissue attachment locations with at least two being separately activated at the selection of an operator to be attached and unattached to an opposing tissue surface. Various means are described for the attachment including vacuum and mechanical attachment. The guide member may have a steering mechanism to remotely manipulate the shape of the guide member. In another embodiment, the ablation member is attached to a reciprocator to move the radiation-emitting member back and forth within the longitudinal pathway over a fixed distance in an oscillating manner to distribute the radiation uniformly in a line. In another embodiment, the reciprocator contains a mechanism for changing the position of the radiation-emitting member in the longitudinal pathway to distribute the radiation over a longer line. In additional embodiments, the invention may include fluid flushing to the ablation member, apparatus to enhance visualization of the ablation procedure and apparatus to monitor and test for transmurality of a created lesion. Transmurality can be assessed to approximate a location of non-transmurality in a formed lesion.

BRIEF DESCRIPTION OF THE DRAWINGS

FIG. 8 is a top, side and front perspective view of an alternative embodiment of the tool of FIG. 2 showing a steering system;

FIG. 9 is a front elevation view of the tool of FIG. 8;

FIG. 10 is a top, side and front perspective view of a further alternative embodiment of the tool of FIG. 2;

FIG. 11 is a front elevation view of the tool of FIG. 10;

FIG. 14 is a bottom, side and front perspective view of a still further alternative embodiment of the tool of FIG. 2;

FIG. 15 is a front elevation view of the tool of FIG. 14;

DETAILED DESCRIPTION OF THE PREFERRED EMBODIMENTS

Figure 1:
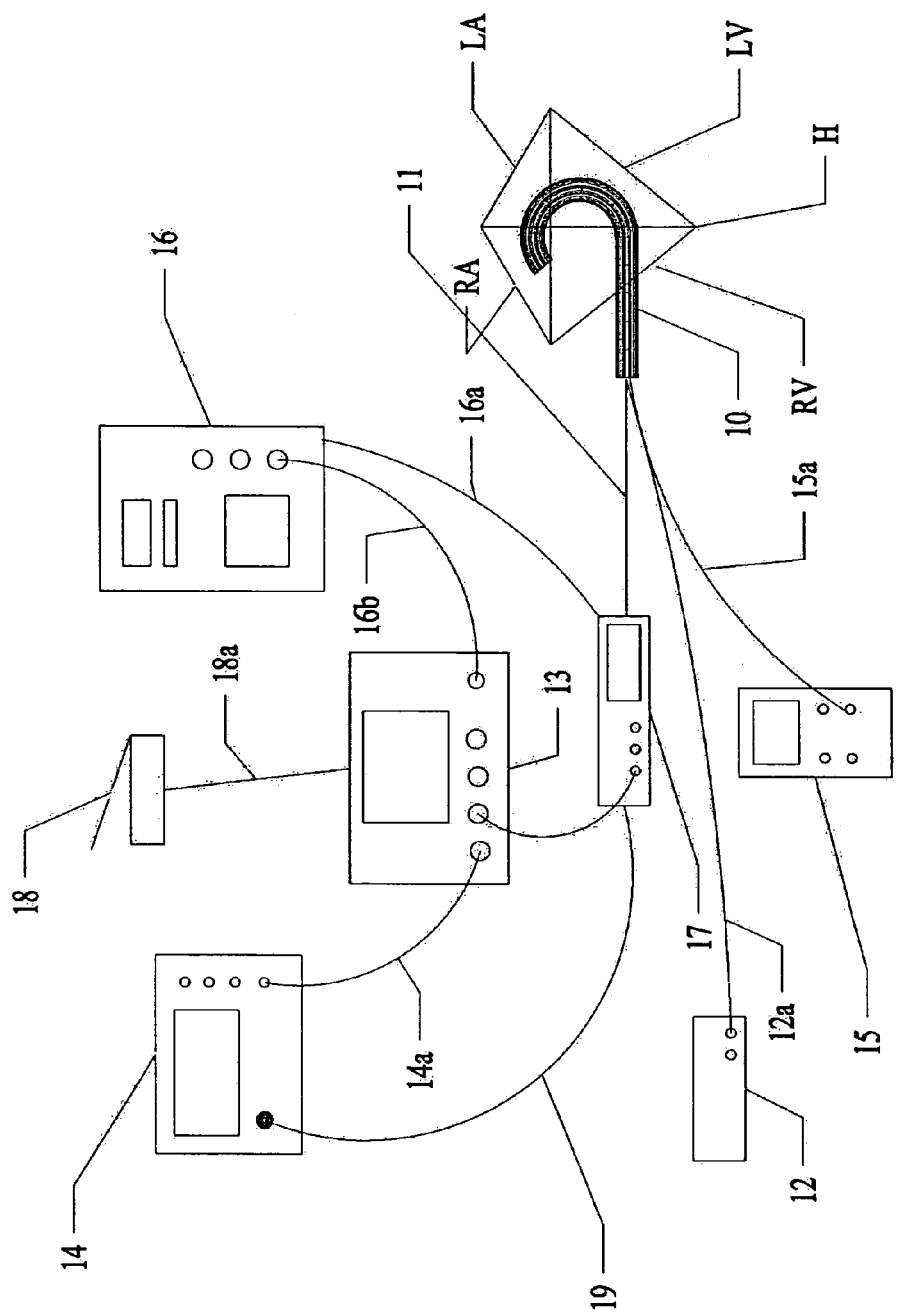
FIG. 1 is a schematic representation of a guided laser ablation tool connected to a laser energy source and a coolant fluid source.

Referring now to the several drawing figures in which identical elements are numbered identically throughout, a description of a preferred embodiment of the present invention will now be provided. In the preferred embodiment, the invention is described as a lesion formation tool for applying laser energy to the epicardial surface of the heart to create a transmural ablation line along the heart. As used in this application, the term "ablation" is used in the context of creating necrosed tissue in the myocardium while avoiding tissue perforation or removal. In the following description, a guide member is described for guiding a lesion formation tool in a MAZE pattern. It will be appreciated the teachings of the present application could be applied to other types of ablation tools (e.g., RF ablation, ultrasound or other). Also, this application may refer to a lesion as "linear". The use of "liner" is not meant to be limited to a straight line but is intended to include a curved or other lesion pattern which is elongated and narrow in width.

Unless otherwise described in reference to a preferred embodiment, all components of the invention can be formed of any suitable material subject to ability of such material to withstand the rigors of sterilization and meet all biocompatibility and other requirements of applicable medical device regulations.

Teachings of Parent Application

The aforementioned U.S. patent application Ser. No. 10/975,674 describes, in detail, a surgical wand for applying laser energy to either the epicardial or endocardial surface of the heart. For treating atrial fibrillation through the MAZE procedure, the wand preferably emits laser energy as coherent light in a wavelength selected to have a very low absorption and very high scatter in myocardial tissue.

Any wavelength suitable to create necrosed tissue in the myocardium without tissue removal could be used. In a preferred embodiment, the wavelength is a near-infrared wavelength selected to have a very low absorption and very high scatter in myocardial tissue. Biological tissue (such as the myocardium) is largely water. Wavelengths in the ranges of between about 470 to about 900 nanometers and between about 1050 to about 1150 nanometers are known to penetrate water with low absorption (e.g., less than about 30% absorption). *Lasers in Cardiovascular Medicine and Surgery: Fundamentals and Techniques*, George S. Abela, M.D., Editor, Kluwer Academic Publishers, 101 Philip Drive, Assinippi Park, Norwell, Mass. 02061 USA, p. 28 (1990). More preferably, the wavelength is selected from the ranges of 790 to 850 nanometers (which range corresponds to commercially available medical diode lasers) and 1050 to 1090 nanometers (which range corresponds to Nd:YAG lasers commonly used in other medical procedures). A laser energy source with a wavelength selected from these ranges will penetrate the full thickness of the myocardium and result in a transmural lesion (i.e., a full-thickness necrosis of myocardial tissue in the atrium). Further such a wavelength minimizes carbonization of the tissue and perforation of the myocardial tissue. Such laser emissions are substantially coherent.

A laser energy source with a wavelength selected from the above ranges will penetrate the full thickness of the myocardium and result in a transmural lesion (i.e., a full-thickness necrosis of myocardial tissue in the atrium). Further, such a wavelength minimizes carbonization of the tissue and perforation of the myocardial tissue. Such laser emissions are substantially coherent.

In the aforesaid '674 application, the wand is a hand-held device with a distal tip placed against either the epicardial or endocardial surface of the heart. The wand is manipulated so that the distal tip moves along the surface of the heart to create a MAZE lesion of a desired pattern. The present invention is directed towards method and apparatus for forming lesions on the heart surface. The invention includes placement of a track on the heart to act as a guide to guide a lesion formation tool in a desired pattern.

Guide Member

With initial reference to FIG. 1, a system is shown for creating at least a portion of a maze pattern on a surface of the heart. FIG. 1 is a schematic illustration of various components to be used in the MAZE procedure.

In FIG. 1, the heart H is shown schematically and divided into left and right atria LA, RA and left and right ventricles LV, RV. A guide member 10 as will be more fully described is shown laying on the epicardial surface of the heart H.

In FIG. 1, the apparatus 10 is shown in a curved configuration for creating a curved lesion pattern on the heart H. It will be appreciated that the curvature pattern shown in FIG. 1 and the size of the apparatus relative to the heart H are greatly exaggerated for ease of illustration.

In a preferred embodiment, the radius of curvatures and the shape of the curvature will be such for placement of the apparatus 10 on a heart H in the proximity of pulmonary veins and other anatomical structures on or near the atria of the heart to create MAZE patterns or only portions of such patterns.

The schematic in FIG. 1 shows supporting apparatus including a vacuum source 12 connected to apparatus 10 by a conduit 12a to create a vacuum in desired chambers of the apparatus 10 as will be described. A power source 14 is connected to an optical fiber 32 for creating desired energy pulses within the laser in the apparatus 10. The fiber 32 feeds into a conduit 30 which is passed into a guide member 20 which is placed on the heart H in a desired pattern. A detailed description of the fiber 30, conduit 32 and guide member 20 will be provided. A reciprocator 17 is provided connected to the conduit 32 for moving the conduit 32 (and contained fiber 32) back and forth in a direction aligned with the fiber axis as will be described.

A pump 16 is shown to connect to a source of cooling fluid (such as saline) via a conduit 16a to the reciprocator 17 for pumping a cooling fluid to the apparatus 10 as will be more fully described. While saline is described as a preferred fluid, it will be appreciated other fluids could be used. For example, a gaseous fluid (such as $CO_2$) could be used instead of a liquid fluid. Such a gas dissipates in the thoracic cavity eliminating the need for suction of a liquid flushing fluid.

An optional electrophysiology signal generator and monitor 15 may be connected via an electrical conductor 15a to electrodes on the apparatus 10 as will be described for the purpose of assessing transmurality of a lesion formed by the apparatus 10. Such a signal generator and monitor are described in the '674 application.

In the description of FIG. 1, it will be appreciated that vacuum sources 12, pumps 16, laser power sources 14, signal generators and monitors 15 and oscillators 17 and connective couplings, cables and tubing are commercially available and form no part of this invention per se. While each of the vacuum source 12, pump 16, laser power source 14 and reciprocator 17 have control knobs and the like, it is convenient to have a separate control module 13 which, through electrical connections 14a, 16b, 17a, controls each of the vacuum source 12, pump 16, laser power source 14 and reciprocator 17. Further, a foot pedal 18 is connected to control module 13 by a conductor 18a. If desired, a physician can use the pedal 18 to control a desired operation parameter hands-free.

Figure 3:
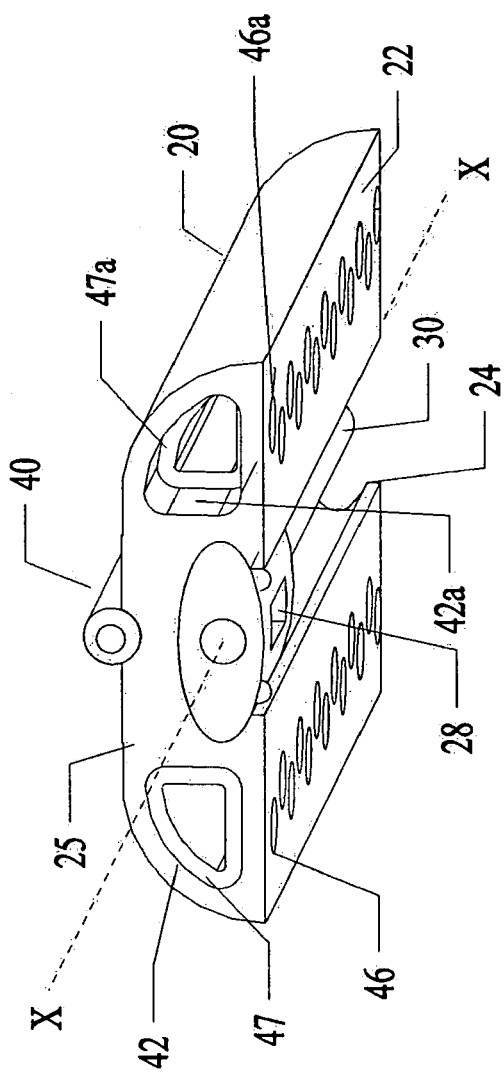
FIG. 3 is a bottom, front and side perspective view of a segment of the tool of FIG. 2.

FIG. 3 illustrates, in perspective view, a length of a segment of the guide apparatus 10. The apparatus 10 includes a guide member 20 of an elongated flexible body and having a generally flat bottom surface 22.

Figure 2:
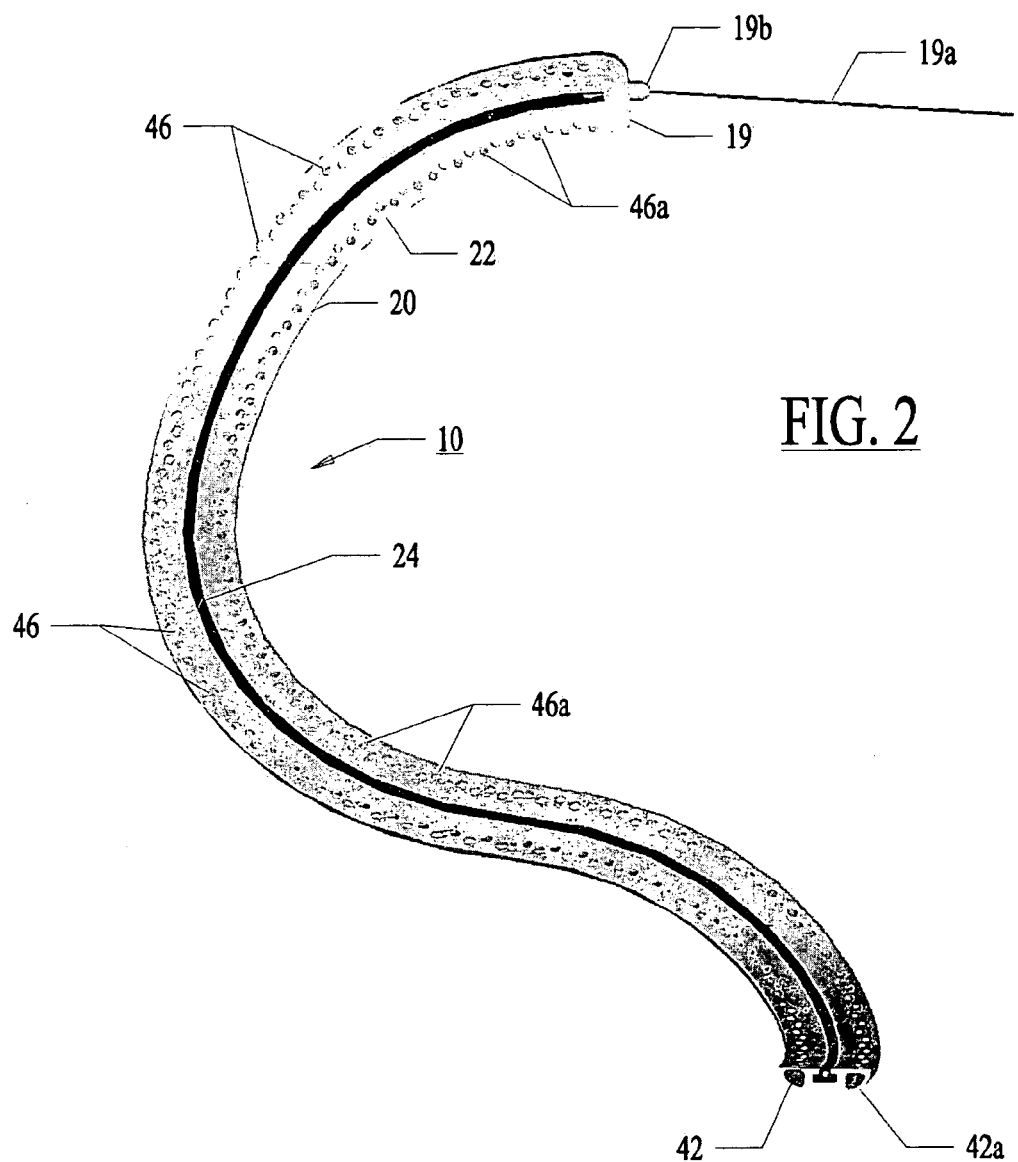
FIG. 2 is a bottom plan view of a guided laser ablation tool according to the present invention.

FIG. 2 is a bottom plan view of the guide member 20. The guide member 20 may have spaced markings along its length to assist in positioning the guide member. A guide channel 24 is formed as a groove centrally positioned within the bottom wall 22 and extending along the longitudinal length of the guide member 20 parallel to a longitudinal axis X-X (FIG. 3). A guide carriage 26 (FIGS. 3, 4, 5-7) is slidably received within the guide channel 24.

FIG. 2 illustrates a pull cord 19a connected to a distal end 19 of the guide member 20 by a strain relief 19b. While it is presently preferred the guide member will be shaped and placed in a desired patter on the heart H with the end 19 on the heart H, it may be desirable to have a very long guide member such that end 19 is pulled through the desired path and tied-off onto an intermediate section or proximal end of the guide member with only an intermediate portion of the guide member in place on the heart in a desired pattern. The cord 19a permits grasping the end 19 and puling it to a desired position as well as securing the end 19 to another structure.

Figure 2A:
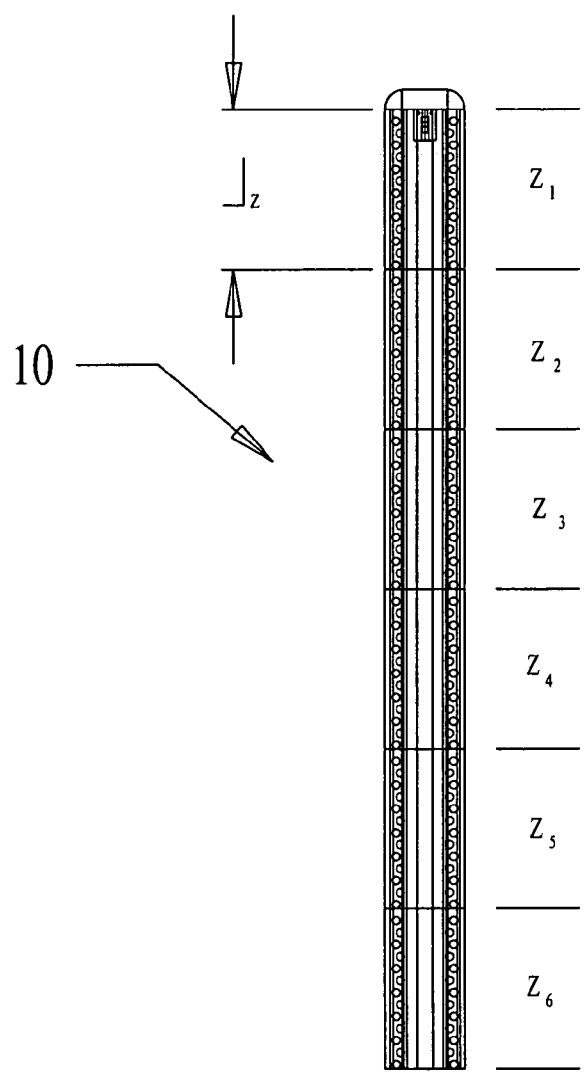
FIG. 2A is a bottom plan view of a guided laser ablation tool according to the present invention with fiber carriage shown and reciprocation zones identified.

FIG. 2A shows the track of FIG. 2 in a straight configuration with guide carriage 26 in guide channel 20 along with six zones, $Z_1$ thru $Z_6$ each of length $L_z$. Length $L_z$ corresponds to the distance the guide carriage travels during reciprocation at a given position of the guide carriage in the reciprocator. Zones $Z_1$ thru $Z_6$ correspond to segments along the guide channel over which the guide carriage can travel with changes in the position of the guide carriage in the reciprocator.

In the embodiment shown, the guide carriage 26 (FIGS. 5-7) is oval in cross section and the guide channel 24 is also oval in cross section. As a result, the guide carriage 26 may axially slide within the guide channel 24 but is prevented from moving transverse to its sliding axis X-X as well as being prevented from rotating about the axis X-X. The carriage 26 includes a bottom opening or window 28. The window 28 may be an open area (as shown) to pass both emitted light and a flushing fluid or may be a closed window of material selected to pass the wavelength of the emitted light.

A flexible fluid conduit 30 is connected to a proximal end of the carriage 26. The conduit 30 moves with the carriage 26 within the channel 24. Pushing the conduit 30 moves the carriage 26 distally. Retraction of the conduit 30 moves the carriage 26 proximally.

An optical fiber 32 passes through the conduit 30. Spacers (not shown) hold the fiber 32 coaxially within the conduit 30 with opposing surfaces of the fiber 32 and conduit 30 defining an annular lumen 34 into which cooling fluid from pump 16 may be passed. The fluid both cools components as well as flushing debris which might otherwise accumulate between the fiber and the epicardial surface.

The fiber 32 is carried in the carriage 26 with a distal tip 33 of the fiber positioned to discharge light through the window 28. Cooling fluid from lumen 34 can also pass through the window 28. To enhance the atraumatic nature of the carriage 26, the carriage 26 is formed of a soft material having a low coefficient of friction or lubricious-like nature against the heart tissue. Also, it is desirable that the material of the tip 24 be as transparent as possible to the therapeutic wavelength. For the preferred wavelengths described above, a preferred material is Delrin® acetal of DuPont Co., New Jersey (USA). While such material is generally transparent to the preferred laser energy wavelengths, the material may absorb some of the energy. Therefore, the fluid flowing through lumen 34 and window 28 acts to cool the carriage 26 and fiber tip 33.

Figure 7:
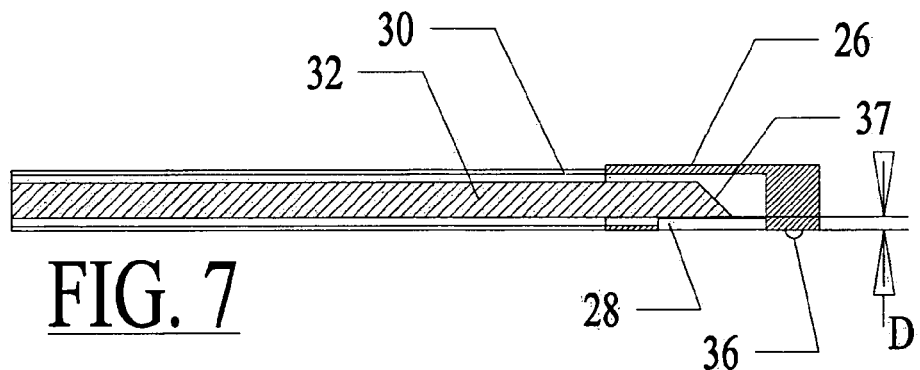
FIG. 7 is a side sectional view of the carriage of FIG. 6.

The light from the fiber 32 passes through the window 28 in a light path generally perpendicular to the axis X-X and the plane of the guide member bottom surface 22. As schematically shown in FIG. 7, the end of the fiber 32 is cleaved, polished and coated for the fiber 32 to a so-called "side fire" laser such that the fiber 32 is not bent. While it is preferred the light from the tip impinge upon the heart tissue at a 90 degree angle, it will be appreciated the angle can be varied and still provide therapeutic benefit. Side-fire fibers are well known. A representative example of such is shown in U.S. Pat. No. 5,537,499 to Brekke issued Jul. 16, 1996 (incorporated herein by reference). The carriage 26 maintains a spacing D between the fiber 32 and the heart surface.

In the embodiment shown, the carriage 26 contains optional sensing electrodes 36 for purposes that will be described. The electrodes 36 may be connected via leads (not shown) to the optional electrophysiology signal generator and monitoring equipment 15.

Figure 4:
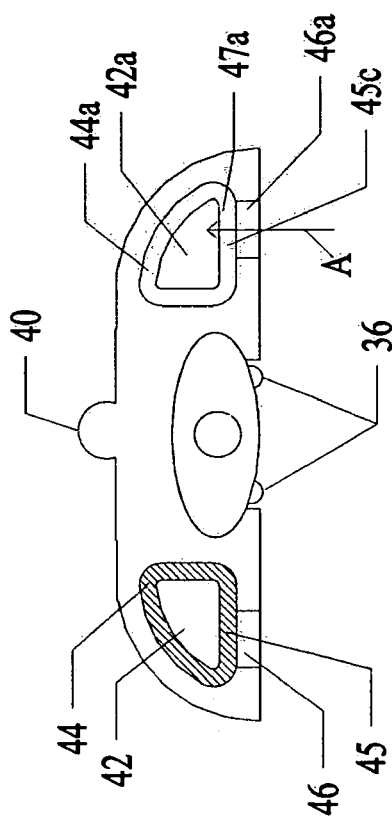
FIG. 4 is front elevation view of the segment of FIG. 2.
Figure 5:
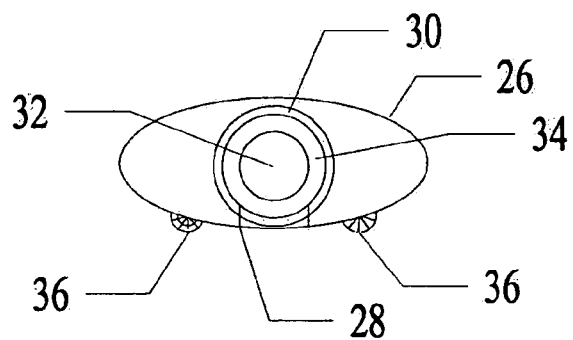
FIG. 5 is a front elevation view of a fiber carriage for use in the tool of FIG. 2.
Figure 6:
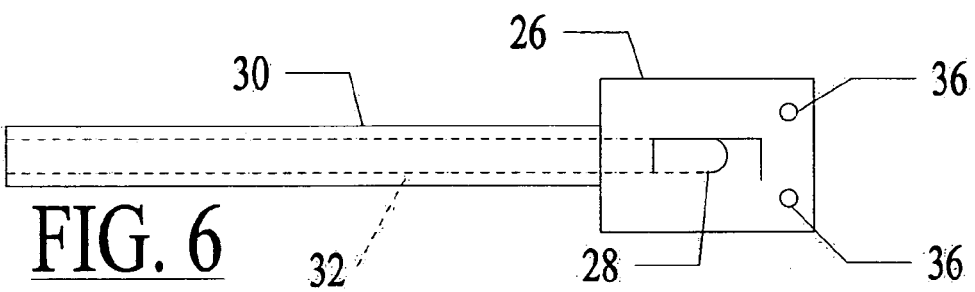
FIG. 6 is a bottom plan view of the carriage of FIG. 5.

Best shown in FIGS. 3 and 4, vacuum plenums 42, 42a are formed throughout the length of the guide member 20 on opposite sides of the guide channel 24. A plurality of vacuum ports 46, 46a are formed through the bottom surface 22 into airflow communication with the plenums 42, 42a.

As will be described, the vacuum plenums 42, 42a and vacuum ports 46, 46a urge the bottom surface 22 against the heart surface and stabilize the guide member 20 during the ablation procedure. While the ports 46, 46a can be applied to a vacuum source at the same time (i.e., all ports simultaneously have a vacuum or none have a vacuum), it may be desirable to control the vacuum so that only some of the ports 46, 46a are under vacuum at any one time. Such control is provided by liners 44, 44a.

The hollow tubular liners 44, 44a are positioned within each of the plenums 42, 42a. The liners 44, 44a terminate at distal ends 47, 47a. Each of the liners 44, 44a is slidable along the longitudinal axis of the plenums 42, 42a. A bottom plate 45, 45a (FIG. 4) of the liners 44, 44a covers the openings 46, 46a.

In a preferred embodiment, the liners 44, 44a are retractable by pulling the liners 44, 44a proximally out of a proximal end of the member 20. As a liner 44, 44a is pulled out of the proximal end of the guide member 20, the liner ends 47, 47a move distally past the holes 46, 46a such that the openings 46, 46a are exposed to the interior of the plenums 42, 42a. The distal openings 46, 46a are exposed to the plenums before more proximal openings 46, 46a.

FIG. 4 illustrates liner 44 positioned with plate 45 covering hole 46 and blocking its communication with plenum 42. Liner 44a is more fully retracted such that end 47a is retracted proximally past hole 46a thereby exposing hole 46a to the plenum 42a. With a vacuum applied to both plenums 42, 42a, only hole 46a would be applying a suction (arrow A in FIG. 4) to the epicardial surface of the heart.

As will be described, the structure permits placement of a distal end 19 of the guide member 20 followed by later securing more distal segments of the guide member to the heart. It will be appreciated this structure and method of operation can be reversed such that liners 44, 44a are pulled from a distal end of the guide member 20 to expose proximal openings 46, 46a to the plenums 42, 42a before expose more distal openings 46, 46a.

Figure 16:
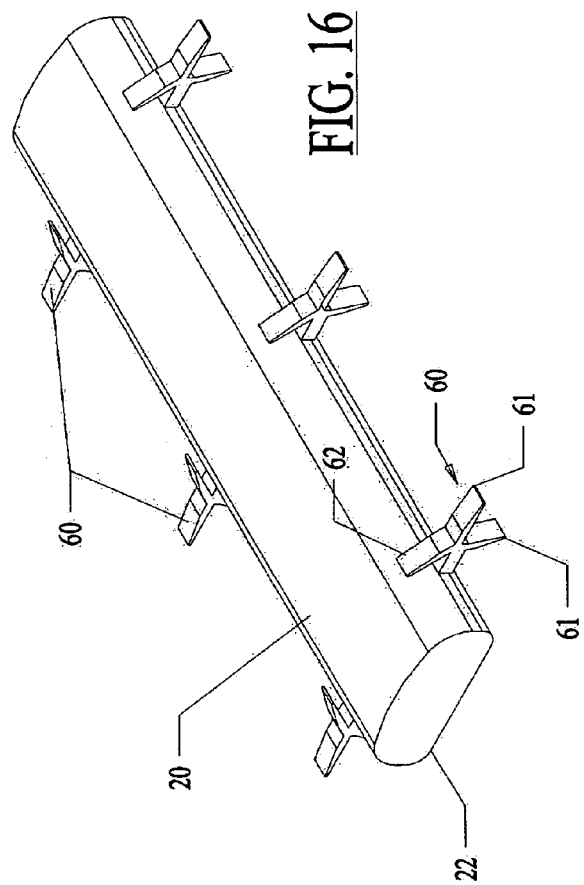
FIG. 16 is a bottom, side and front perspective view of a yet further alternative embodiment of the tool of FIG. 2.
Figure 17:
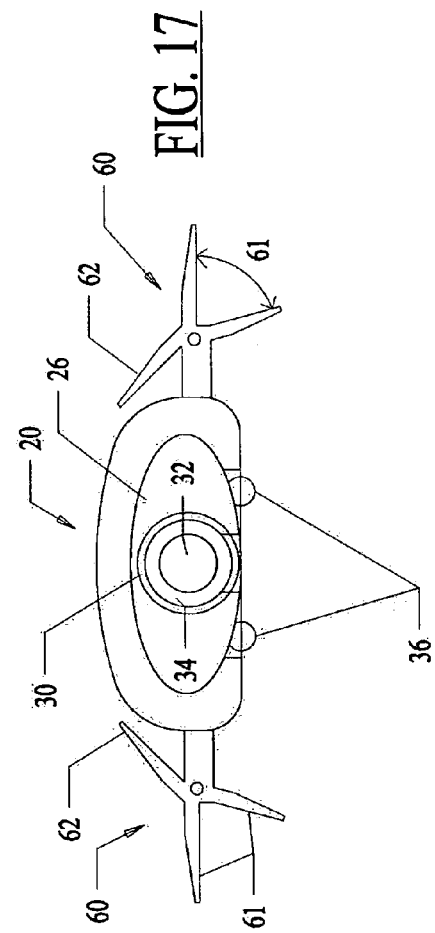
FIG. 17 is a front elevation view of the tool of FIG. 16.

While a vacuum is preferred for releasably securing the guide member 20 to the heart surface, other attachments options are possible. For example, FIG. 16 shows an alternative mechanism for attaching the guide member 20 to an epicardial surface of the heart. Instead of a vacuum attachment as described above, FIG. 20 illustrates use of so-called "bulldog" clamps 60 positioned along the side edge of the guide member 20. The bulldog clamps may be separately actuated during surgery to attach to the surface of the heart and hold the guide member in fixed position on the heart. Such clamps are well known. An example of such is a Vascu-Statt® Single-Use Bulldog Clamp sold by Scanlan International, One Scanlan Plaza, Saint Paul, Minn. USA for use in vascular occlusion and as described at web page http://www.scanlaninternational.com/singleuse/vascustatt.asp. The clamps have jaws 61 which engage tissue. The jaws 61 are actuated by a lever 62.

Figure 23:
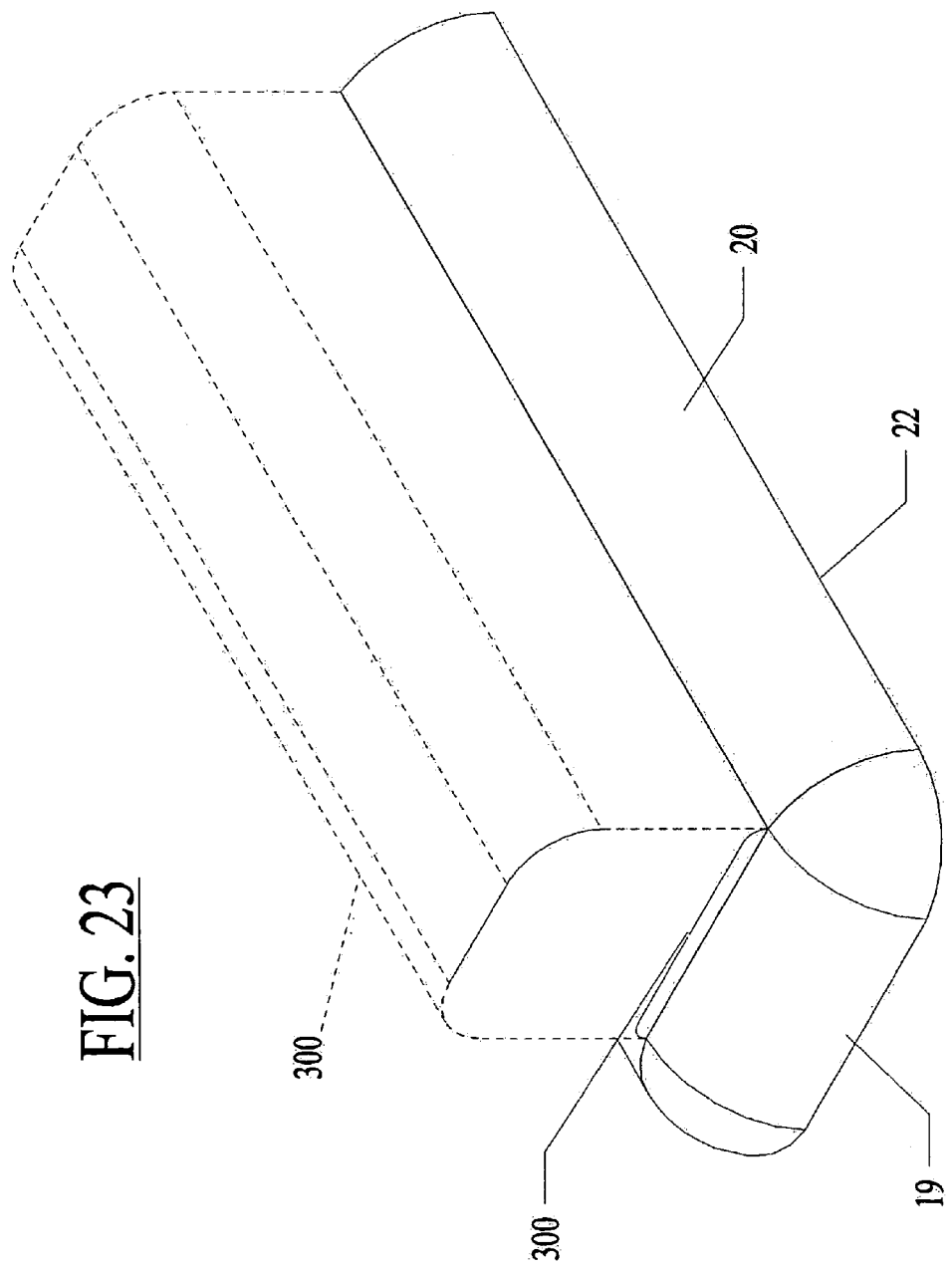
FIG. 23 is a view of a guide member showing an optional balloon to urge the guide member against a heart surface.

FIG. 23 illustrates a still further embodiment for urging the lower surface 22 of the guide member 20 against a heart surface. An upper surface of the guide member is provided with an inflatable balloon 300 extending at least partially along its length. In FIG. 23, the balloon is shown deflated in solid lines and inflated in phantom lines. The guide member 20 is placed between the heart surface and the pericardium when the balloon 300 is deflated. When the guide member 20 is in the desired position, the balloon 300 is inflated. The inflated balloon 300 urges against the pericardium to urge the bottom surface 22 against the heart surface.

Placement of Guide Member and Formation of MAZE Lesions

During placement of the guide apparatus 10 on the heart H, the liners 44, 44a can be fully inserted within the plenums 42, 42a and a vacuum applied to the interior of the plenums 42, 42a. The vacuum does not communicate with the holes 46, 46a since the liners 44, 44a are covering the holes 46, 46a.

With the highly flexible member 20, the distal end 19 (FIG. 2) can be placed in any suitable manner in a desired location on the heart surface. Later in this application, various techniques will be described for shaping or steering the guide member 20 to assist a physician in this placement.

With the distal end 19 so positioned, it is releasably secured to the heart surface by retracting the liners 44 to expose the most distal holes 46, 46a with the vacuum urging the surface 22 against the heart. With the distal end secured, intermediate portions of the guide member 20 may be placed in a desired location on the surface of the heart. When the surgeon is satisfied with the positioning, the liners 44 are further retracted causing holes 46, 46a of the intermediate portions to be exposed to the vacuum and thereby securing the device 20 to the heart at those locations. This process can be sequentially repeated until the entire guide member 20 is placed in its desired positioning and pattern on the heart. The desired pattern of the guide member 20 corresponds with a position of a portion of a desired MAZE pattern lesion to be formed by the ablation member which, in the preferred embodiment, is the tip 33 of the laser fiber 32.

So positioned, the carriage 26 may be moved within the guide channel 24 and the laser fiber 32 may be energized by activating power source 14 to form a transmural lesion in the heart wall. The conduit 30 is pushed or pulled as desired to move the carriage 26 distally or proximally, respectively, thereby moving the fiber tip 33 in a desired pattern over the epicardial surface of the heart. The physician moves the carriage along the exterior surface of the heart in order to create lines of ablated (i.e., non-electrically conducting) tissue by raising the temperature of the cardiac tissue to that required to achieve cellular death (typically about 55° C.). It is presently estimated that, with an operating laser power of about 25 watts, a surgeon can create an ablation line by gliding the moving the carriage 26 over the heart surface at a rate of between about 1 to 5 cm of linear travel per minute. By way of non-limiting example, with a diode laser, power can range from about 5 to about 50 Watts.

While a lesion can be formed by pulling the fiber 30 distally in one pass, it is presently preferred to form the lesion in zones. For example, a desired lesion pattern can be divided into multiple zones. Within a zone, the energized fiber tip 33 is moved back and forth with carriage 26 in the guide member 20 multiple times to apply a desired dosage of energy to tissue in the zone (FIG. 2A). The carriage 26 and fiber tip 33 are then moved to the next zone and the procedure is repeated.

With the structure thus described, it has been shown how the guide member 20 guides the laser tip 33 in the desired MAZE pattern. Further, throughout this patter, the carriage 26 holds the laser tip 33 in a constant spacing (D in FIG. 7) from the epicardial surface of the heart. The guide member 20 maintains a desired spacing between the end of the ablation tool (i.e., the fiber tip 33 in a preferred embodiment) and the surface of the heart throughout the length of the guide member 20 and avoids direct contact of the ablation member and the heart.

It is desirable to have as close a spacing D (FIG. 7) of the fiber discharge tip 33 to the bottom wall 22 of the guide member 20 as possible to maximize laser energy penetration of myocardial tissue. The power density impinging on cardiac tissue decreases rapidly with increasing spacing D. However, a small spacing D (about 0.25 mm preferred) from the surface of the heart is desirable to prevent coagulation of biological products onto the face of the optical fiber. Build-up of tissue is undesirable. It can cause carbonization and spalling of the optical fiber face which reduces laser energy output from the optical fiber. If sufficient biological material is present in the vicinity of the optical fiber face, overheating and subsequent melting of components can occur. Due to the unobstructed path from the fiber tip 33 to the heart surface, the light is a non-diffused or unmodified beam directed at the heart surface either perpendicularly of at an angle as described above.

The flow of coolant fluid from the window 28 cools the material of the carriage 26, washes biological material (e.g., blood, tissue debris or the like) from the light path between optical fiber tip 33 and the heart surface, and acts as a lubricant to further facilitate atraumatic gliding movement of the carriage 26 over the surface of the heart.

The washing action of the fluid maximizes the laser energy impinging on the surface of the heart. Additionally, this fluid provides a means to cool the tissue in the region of the carriage 26 to help ensure that tissue carbonization and subsequent vaporization of cardiac tissue do not occur. This substantially reduces the likelihood of perforation of the heart wall. Also, the fluid forms a protective layer at the discharge tip 33 of optical fiber 32 which reduces the likelihood biological residue will impinge on and/or adhere to the discharge tip 33 which can otherwise cause spalling of the fiber tip 33 and reduce optical transmission of laser energy.

Since the fluid flows into the body of the patient, the fluid should be medical grade and biocompatible. Also, the fluid should have a low absorption of the laser energy. A preferred fluid is a physiological saline solution which may be supplied at ambient temperature.

The pump 16 (FIG. 1) output is controllable. Its controls are integrated into the control module 13 to permit an operator to set or modify a flow rate of the fluid. For example, an operator can set fluid flow as low as 0.2 milliliters per minute or as high as 20 milliliters per minute or any other desired setting. As will be described, some flow is preferred to cool the tip 33 and wash the end of the fiber 32. Further, as the fluid flows between the carriage 26 and the heart, the fluid acts as a lubricant further facilitating atraumatic gliding motion of the carriage 26 over the heart surface. For treating thin atrial tissue, the flow rate is preferably about 10 milliliters per minute which provides the afore-mentioned benefits but minimizes excessive fluid infusion into the patient.

Evaluating Transmurality of Lession

During the ablation process or thereafter, the electrodes 36 may be energized to test conductivity across the formed lesion to ensure transmurality as taught in the '674 application. The electrodes 36 are selected and adapted to sense an electrical potential in the local area of each.

Upon completion of the ablation procedure described above, the surgeon can move the carriage 26 back through the channel 24. Securing the guide member 20 to the heart as described ensures the electrodes 36 are positioned on opposite sides of the lesion line formed during the ablation procedure.

During this retracing step, electrical stimuli are then transmitted to the electrodes 36 from electrophysiology monitoring equipment or similar instrumentation 15 which are connected to the electrodes 26 by electrical conductors (not shown) formed into the conduit 30 and carriage 26.

The response of the cardiac tissue is observed. Tracing the created lines in this manner allows the surgeon to test the timing of the signal propagation between the two electrodes, the cardiac potential, or the potential across the two electrodes at different locations along the ablation line. Delayed or lengthened signal timing and/or altered potentials across the electrodes in a given region can indicate that a complete blockage of electrical energy transmission has been obtained. In the event a shortened timing of signal propagation between the electrodes or a drop in the potential across these electrodes is measured (indicating a lower impedance), the procedure of applying laser energy to the surface of the heart may be repeated as necessary until the desired effect of electrical block is obtained. As an alternative to retracing the lesion, the electrodes 36 can be activated to test transmurality as the lesion is formed.

In previously described embodiments (e.g., with reference to FIG. 3), sensing electrodes 36 were placed on the carriage and movable with the carriage. FIGS. 14 and 15 illustrate an alternative embodiment. In these Figures, the vacuum plenums, liners and suction holes are not shown for ease of illustration.

In FIGS. 14 and 15, sensing electrodes 36' are placed on the bottom wall 22 of guide member 20 extending along the length of the guide member. The electrodes are fixed in place and are not movable with the carriage 26. Instead, after a MAZE pattern is formed, the electrodes 36' may be energized to test for conductivity across the formed lesion.

With reference to FIGS. 25 through 31, a more focused method for assessing transmurality is presented. In the prior art, gross techniques are described for assessing transmurality of a lesion in a MAZE procedure. See, e.g., Van Brakel, et al., "Evaluation of Epicardial Microwave Ablation Lesions: Histology Versus Electrophysiology", *Ann. Thorc. Surg.*, Vol. 78, pp. 1397-1402 (2004). The Van Brakel, et al., article describes forming a lesion around the pulmonary veins (as illustrated in FIG. 1 of the article) to create a bounded area of tissue around the pulmonary veins separated from the remainder of the atrial tissue by an enclosed lesion line.

In Van Brakel, et al., efficacy of the transmurality of the lesion is assessed by placing a pacing electrode on the tissue within the bounded area. A pickup electrode is placed on the atrial tissue outside of the bounded area on an opposite side of the lesion line. A pacing signal is applied to the bounded area. If no responsive signal is sensed by the pickup electrode, the lesion is presumed to be a continuous and transmural lesion surrounding the pulmonary veins. If a pickup signal is detected, the lesion is presumed to be either non-continuous or non-transmural resulting in a complete reapplication of the ablation in a complete lesion line around the pulmonary veins.

In Van Brakel, et al., no attempt is made to identify or approximate a specific location of the gap in the lesion line or the region of non-transmurality. This is undesirable since the recreation of an entire lesion line requires delivery of excess and unnecessary ablation energy that may lead to tissue carbonization, perforation or reduced atrial transport function without addressing the region of insufficiency. Also, it is difficult to maintain a lesion forming apparatus in a fixed location on a heart for any extended period of time (for example, as little as 5 to 10 additional minutes), since the heart is beating continuously and it is easy to unintentionally move the ablation tool or any guide member on the heart.

A gross test for transmurality is also described in Fuller, et al., "Intramural Coronary Vasculature Prevents Transmural Radiofrequency Lesion Formation", *Circulation*, pp. 1797-1803 (2003). The Fuller, et al., article describes clamping atrial tissue in close proximity to the pulmonary vein while creating an ablation at the pulmonary vein with an RF (radio-frequency) ablation tool. Ablation is continued until the measured conductance (or, inversely, impedance) drops to an acceptable level. Again, no attempt is made to identify any location of a potential gap in a lesion to permit re-ablating only the area or region of the gap.

U.S. Pat. No. 6,546,935 to Hooven, et al., issued Apr. 15, 2003 describes a clamp electrode for the pulmonary veins and describes assessment of the ablation formed by the electrode. Such a system is also shown in U.S. Pat. No. 6,517,536 to Hooven, et al., issued Feb. 11, 2003. U.S. patent application Publication No. US 2005/0075629 A1 published Apr. 7, 2005 describes a method for assessing tissue ablation transmurality including a probe which penetrates into tissue. U.S. Pat. No. 6,068,629 to Haissaguerre, et al., issued May 30, 2000 describes tissue mapping and ablation. Standard electrophysiologic mapping incorporates electrode arrays for qualifying percutaneous catheter ablations as well as for diagnosing different cardiac arrhythmias.

Figure 25:
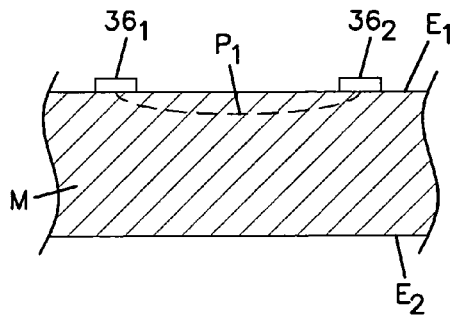
FIG. 25 is a schematic cross-sectional view of a myocardial tissue which transmurality assessment electrodes placed on an epicardial surface.

FIGS. 25 through 34 illustrate a method according to the present invention utilizing the electrodes previously described for approximating a location of a discontinuity in a lesion line or a region in a lesion which is not transmural. FIG. 25 shows electrodes 36$_1$ and 36$_2$ placed on the epicardial surface E$_1$ of the myocardium M. It will be appreciated that lesion assessment can also be performed from the endocardial surface E$_2$ of the myocardium M.

The electrodes 36$_1$ and 36$_2$ are identical to electrodes 36 previously described. As previously described, the electrodes 36$_1$ and 36$_2$ may be either mounted on the carriage 26 or mounted on the bottom wall of the guide member 20 (or by applied to the heart by any suitable separate tool such as an electrode-tipped probe).

FIG. 25 illustrates, in cross-section, the myocardium M without a lesion formed in the myocardium. Accordingly, the conductivity of the myocardial tissue has not been altered by formation of a lesion. A signal is applied to the first electrode 36$_1$ by the equipment 15 of FIG. 1. A responsive signal is picked up by electrode 36$_2$ with the signal returned to the monitoring equipment 15 for analysis. With no lesion in the myocardium M, the signal path P$_1$ is predominantly near the epicardial surface E$_1$ taking the path of least resistance between the electrodes 36$_1$, 36$_2$. This results in a very short period of time elapsing from the point of applying the signal at electrode 36$_1$ to receiving the signal at electrode 36$_2$.

Figure 26:
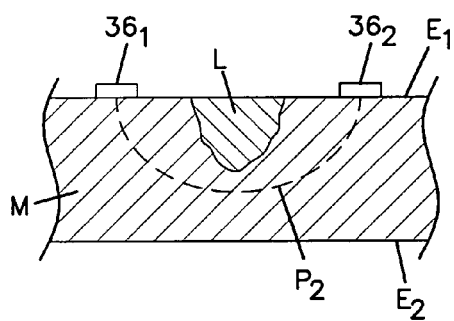
FIG. 26 is the view of FIG. 25 with a non-transmural lesion formed in the tissue.

FIG. 26 illustrates a lesion L formed only partially through the myocardium and extending from the epicardial surface E$_1$ and only partly extending toward the endocardial surface E$_2$. The lesion L of FIG. 26 would be an undesirable non-transmural lesion. When the signal is applied to electrode 36$_1$, the signal path to electrode 36$_2$ is the longer path P$_2$ resulting in a slightly longer period of time between the time of application of the signal to electrode 36$_1$ and the pickup of the response signal at electrode 36$_2$.

Figure 27:
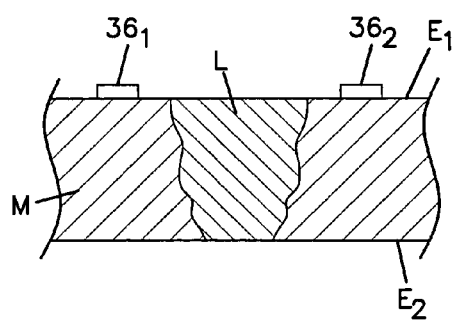
FIG. 27 is the view of FIG. 25 with a transmural lesion formed in the tissue.

FIG. 27 illustrates a desired, fully transmural lesion L formed throughout the wall thickness of the myocardium M. Due to the non-conductivity of the lesion L, no signal passes to electrode 36$_2$ upon application of a signal to electrode 36$_1$.

Figure 28:
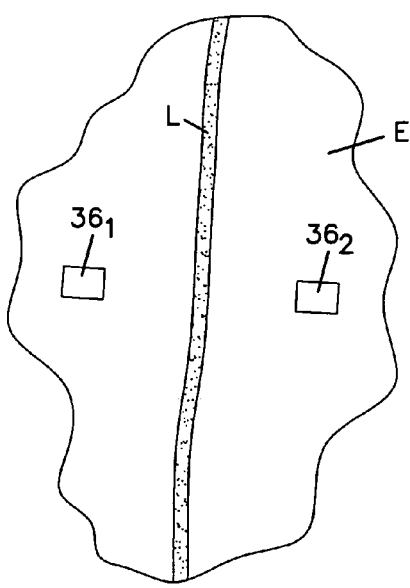
FIG. 28 is a schematic plan view of a portion of an epicardial surface showing a formed lesion and showing placement of transmurality assessment electrodes.
Figure 28A:
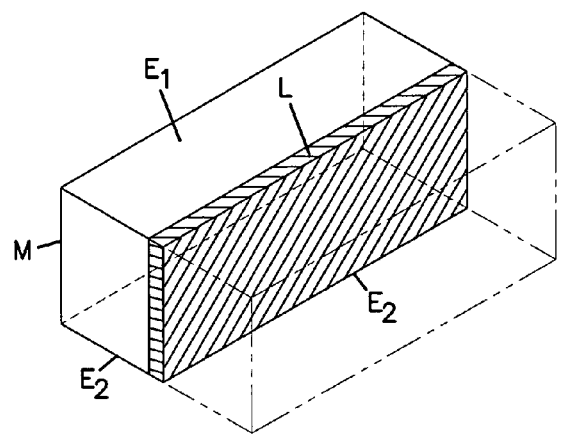
FIG. 28A is a perspective view of the lesion of FIG. 28 without showing the transmurality assessment electrodes.

FIGS. 25 through 27 illustrate the alteration of the signal pathway $P_1$, $P_2$ in response to the depth of lesion formation in the myocardium. A lesion may also be formed which is not continuous along its length. For example, FIGS. 28 and 28A illustrate a desired lesion L which is continuous along its length and in the example of FIGS. 28 and 28A, fully transmural along its length. As a result, upon application of a signal to electrode $36_1$, a responsive signal is detected at electrode $36_2$ with a long time delay. If lesion forms a totally isolated region in the heart, then no responsive signal would be detected at electrode $36_2$ upon completion of the isolating lesion.

Figure 29:
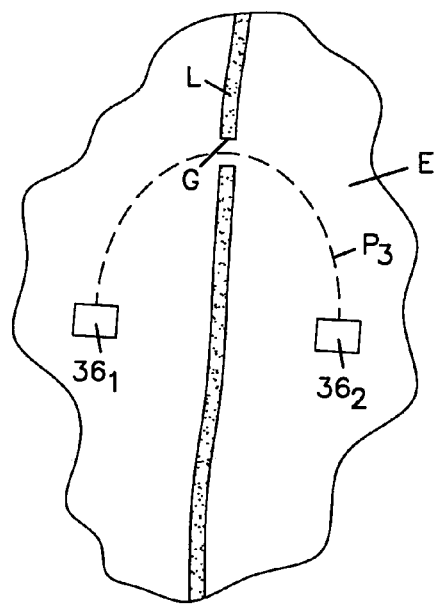
FIG. 29 is the view of FIG. 28 showing a non-transmural gap in the lesion in close proximity to the electrodes.
Figure 29A:
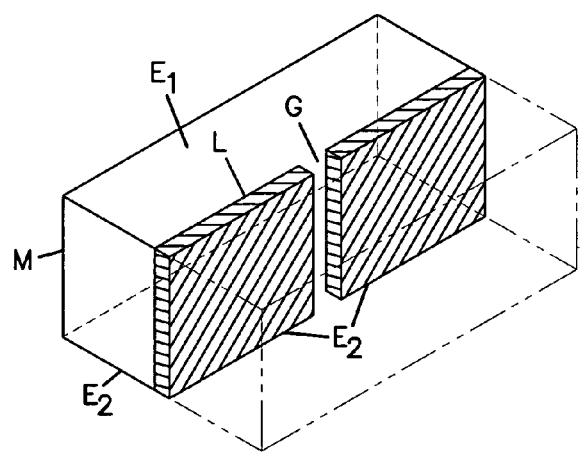
FIG. 29A is a perspective view of the lesion of FIG. 29 without showing the transmurality assessment electrodes.
Figure 29B:
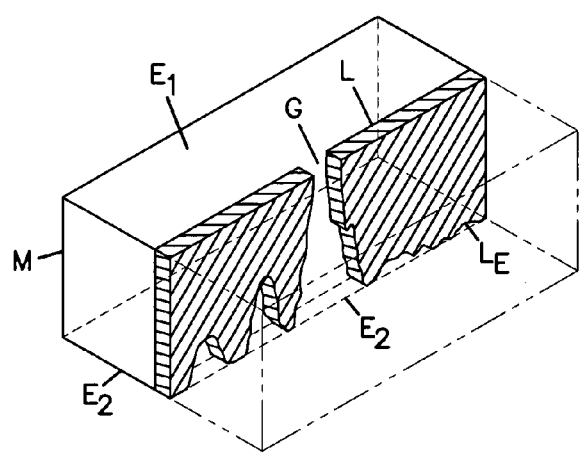
FIG. 29B is the view of FIG. 29A showing a non-transmural lesion with a discontinuity gap as well as having portions of the lesion which do not extend through the full thickness of the myocardium.
Figure 30:
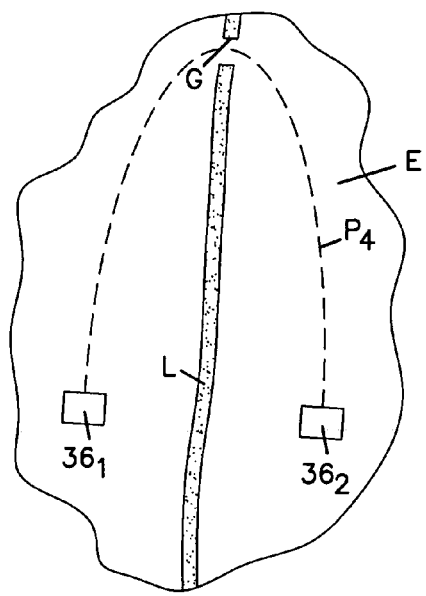
FIG. 30 is the view of FIG. 29 showing the gap further spaced from the electrodes.

FIGS. 29 and 29A illustrates a gap G in the lesion L in close proximity to the electrodes $36_1$, $36_2$ resulting in a signal path $P_3$ extending between the electrodes. FIG. 30 illustrates the positioning of the gap G substantially spaced from the electrodes relative to the spacing in FIG. 29. As a result, much longer signal path $P_4$ is formed. Accordingly, in FIG. 33 a much longer time interval results for a signal to pass from electrode $36_1$ to electrode $36_2$ in FIG. 30 than in FIG. 29. It will be appreciated that the gap in FIGS. 29 and 30 need not be a full transmural gap but could represent a non-transmural lesion where the gap occurs near the endocardial surface and the lesion may be continuous near the epicardial surface (in the event the ablation tool is passed over the epicardial surface). FIG. 29B illustrates a lesion which includes a gap G as well as portions of the lesion L not extending through the full thickness of the myocardium. A gap G may be referred to as a discontinuity. As used herein, the term non-transmural is intended to include discontinuities.

Figure 31:
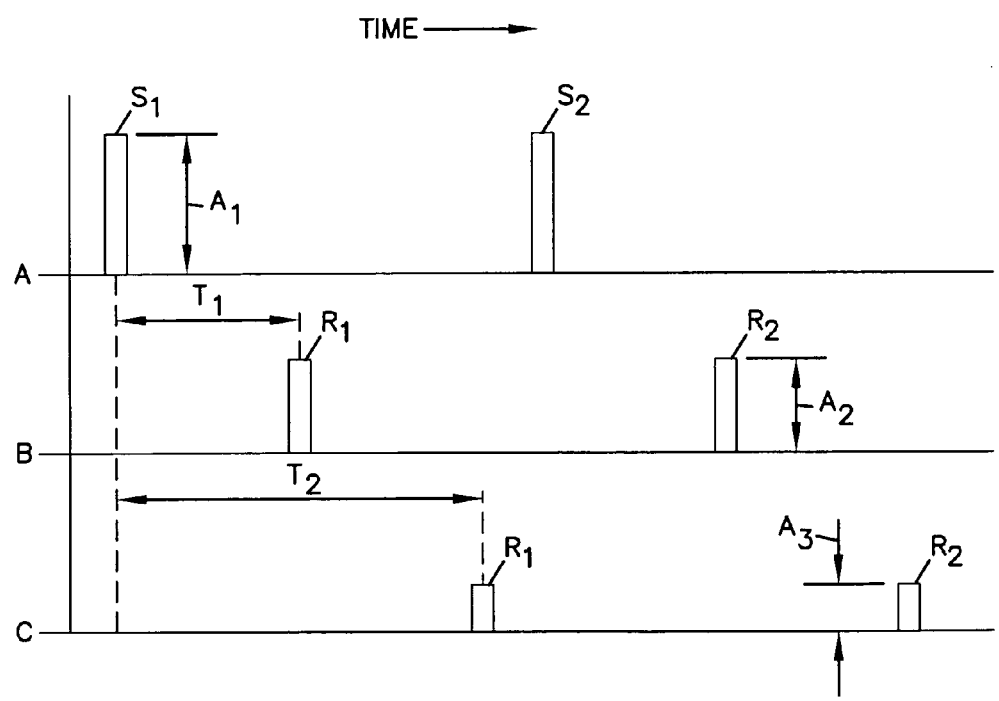
FIG. 31 is a graphical representation showing response of a transmurality assessment signal varying with a distance of a non-transmural gap to the transmurality assessment electrodes.

The consequence of the additional time for a signal to pass between the electrodes $36_1$ and $36_2$ in response to a distance of the electrodes from a discontinuity or non-transmural gap in the lesion is graphically illustrated in FIG. 31. Line A illustrates signals $S_1$ and $S_2$ applied to electrode $36_1$ at timed intervals. Line B illustrates a signal response received by electrode $36_2$ in response to the signals $S_1$ and $S_2$. It will be noted that the timing of the input signals $S_1$, $S_2$ and their associated response signals $R_1$ and $R_2$ are offset by a time delay $T_1$.

In line C, the response signals $R_1$, $R_2$ are spaced from the input signals $S_1$, $S_2$ by a longer time interval $T_2$. Accordingly, a response according to line B would indicate a non-transmural or non-continuous lesion portion in close proximity to the electrodes $36_1$, $36_2$ while a response of line C would indicate a substantially greater distance between the non-transmurality location and the electrodes $36_1$, $36_2$ (such as that illustrated in FIG. 30). Accordingly, utilizing and assessing the time difference between the input signals $S_1$, $S_2$ and the response signals $R_1$, $R_2$ permits approximating a general location of the non-transmurality lesion with respect to the location of the electrode pairs $36_1$, $36_2$.

While a change in response time is a most preferred parameter for assessing transmurality, other signal parameters may be used. For example, the waveform of the signal can be indicative of a transmural lesion. While waveforms are complex, for the ease of illustration, a modification of the waveform is illustrated in FIG. 31 as an alteration of amplitude. In FIG. 31, it will be noted that the amplitude $A_2$, $A_3$ of the response signals is smaller than the amplitude $A_1$ of the input signals and that such amplitude decreases with respect to the spacing of the electrodes $36_1$, $36_2$ from the gap in the lesion.

Another example is measuring and assessing the signal from a prospective of impedance or conductance or waveform alteration in lieu of time delay from the input signal to the response signals. By sending an electrical signal through electrode $36_2$ with a different waveform and frequency from that of the heart, it is possible to measure the impedance of tissue between electrodes $36_1$ and $36_2$. The propagation of this signal no longer depends on the underlying depolariziation cycle of cardiac cells but the bulk electrical properties of cardiac tissue. Therefore, this measurement can be made while the heart is in atrial fibrillation or in normal sinus rhythm. In addition, measurement of the bulk electrical property of tissue must also be done within short distances between electrodes. Therefore, this method is ideally suited to make transmurality measurements concurrent with ablation.

Figure 32:
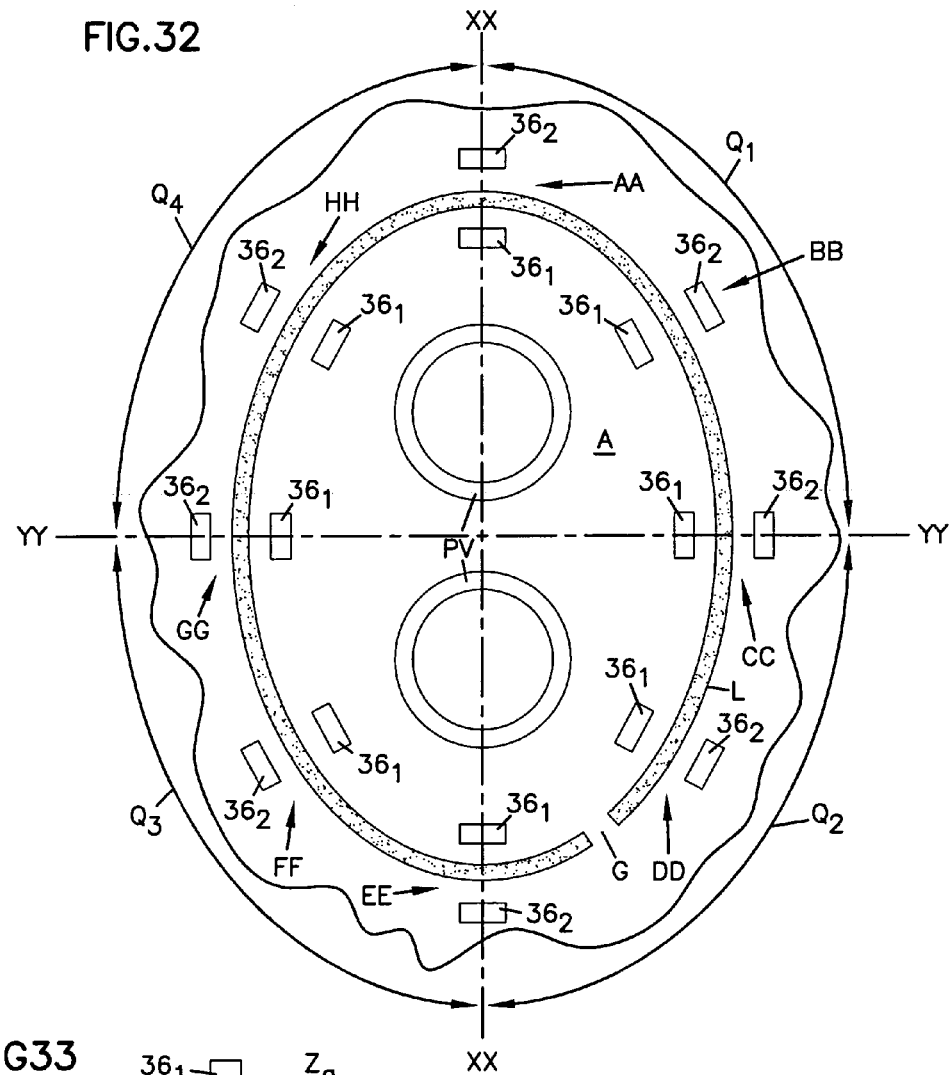
FIG. 32 is a schematic plan view of a portion of an epicardial surface and showing a formed lesion surrounding pulmonary veins and showing placement of a plurality of pairs of transmurality assessment electrodes.

FIG. 32 illustrates the use of the delay signal responses in an embodiment for measuring the continuity and transmurality of a lesion formed around pulmonary veins PV. As shown in FIG. 32, a lesion L is formed as a continuous lesion around the pulmonary veins to define a bounded area A includes the pulmonary veins surrounded by the lesion.

A plurality of pairs (AA-HH) of electrodes $36_1$, $36_2$ is positioned evenly spaced around the perimeter of the lesion L. Electrodes $36_1$ are positioned within the area A bounded by the lesion L. Electrodes $36_2$ are positioned outside the area A. The greater the number of electrode pairs AA-HH, the greater the accuracy in assessing the location of any detected gap G or non-transmural lesion segment. For a full lesion surrounding the pulmonary veins PV, such a lesion might have a path length of about 20 to 30 centimeters. In a preferred embodiment, it is presently anticipated to have electrode pairs placed at every 2 centimeters along the length of the lesion L for a total of 10 or 15 pairs of electrodes (only 8 such pairs AA-HH being shown in FIG. 32 for ease of illustration). Since the location of the pairs are known, the pairs AA-HH can divide the lesion L into zones illustrated in FIG. 32 as quadrants Q1-Q4 divided by axes XX-XX and YY-YY.

Each of the pairs AA-HH can receive an input signal at a first electrode $36_1$ of the pair and with the associated electrode $36_2$ receiving a response and noting a time delay between the input signal and the response signal. After each such pair is individually tested in the same manner, a location of non-transmurality can be approximated. Such location will be nearest the electrode pairs having the shortest time delay and furthest from the electrode pairs having the longest time delay. Accordingly, the invention permits identifying a much smaller segment (for example, the quadrant) of the lesion which is suspect of having a discontinuous lesion gap resulting in the need to only re-ablate the suspect quadrant. This substantially reduces the amount of time needed to re-do lesion formation in an already time critical procedure.

In the example of FIG. 32, a non-transmural gap G is shown in the lesion L in quadrant $Q_2$ between electrode pairs DD and EE. The time delay between an input signal and response signal will be shortest at electrode pairs DD and EE. Moving clockwise (in the view of FIG. 32) from electrode pair EE, the time delay will get progressively longer for electrode pairs FF through HH. Similarly, moving counter-clockwise (in the view of FIG. 32) from electrode pair EE, the time delay will get progressively longer for electrode pairs DD through AA. This analysis will indicate the gap G is in quadrant $Q_2$ and necessitate re-ablation only in quadrant $Q_2$.

FIG. 32 illustrates assessing a lesion after complete formation of the lesion. In FIG. 32, the electrodes $36_1$, $36_2$ are preferably mounted on a guide member 20 as previously disclosed such that the guide member 20 may be held in a desired place on the heart and, if a re-ablation is required in a particular quadrant, the ablation member (i.e., laser tip 33) can be moved in the fixed guide member 20 to the quadrant and the lesion reformed.

Figure 33:
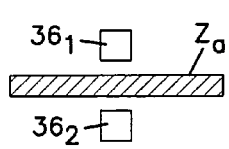
FIG. 33 shows a first lesion segment zone with a pair of transmurality assessment electrodes on opposite sides of the first zone.
Figure 34:
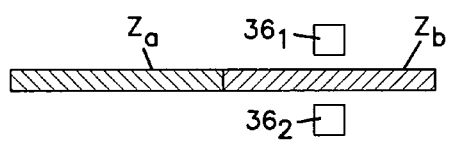
FIG. 34 is the view of FIG. 33 after formation of a second lesion segment zone with a pair of transmurality assessment electrodes on opposite sides of the second zone.
Figure 35:
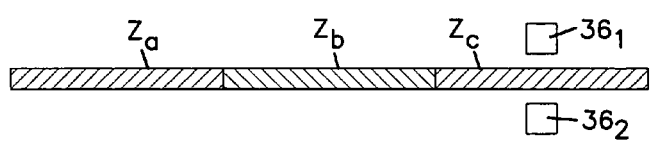
FIG. 35 is the view of FIG. 34 after formation of a third lesion segment zone with a pair of transmurality assessment electrodes on opposite sides of the third zone.

FIGS. 33 through 35 illustrate forming a lesion by testing transmurality of a lesion segment before moving on to form a new lesion segment. For example, in FIG. 33 a lesion segment or zone $Z_a$ is formed. As described elsewhere in this application, the ablation member can be moved back and forth within the zone to apply the amount of energy estimated to form a transmural lesion. After such formation, the electrodes $36_1$, $36_2$ are used to determine transmurality of the lesion zone $Z_a$ by applying an input signal to electrode $36_1$ and measuring a response at electrode $36_2$. The time delay is noted for acceptability to determine if the formed lesion segment $Z_a$ is within any prescribed tolerances for a confidence of transmurality.

After formation of such lesion $Z_a$, the ablation member is moved to a contiguous segment to form a second lesion segment $Z_b$. After formation of the second lesion zone $Z_b$ the electrodes $36_1$, $36_2$ are placed apart centrally within the zone $Z_b$ and transmurality is tested as previously described with reference to FIG. 33. If zone $Z_b$ does not provide a response signal of sufficiently long duration, zone $Z_b$ is presumed to be non-transmural and the ablation is repeated until the desired response time is achieved. Then, the ablation member is moved on to the third contiguous zone $Z_c$ and the procedure is repeated. Accordingly, a plurality of lesion segments are successively formed with transmurality assessed at each lesion segment before moving on to the next, contiguous lesion segment.

Endoscopic Visualization

Figure 12:
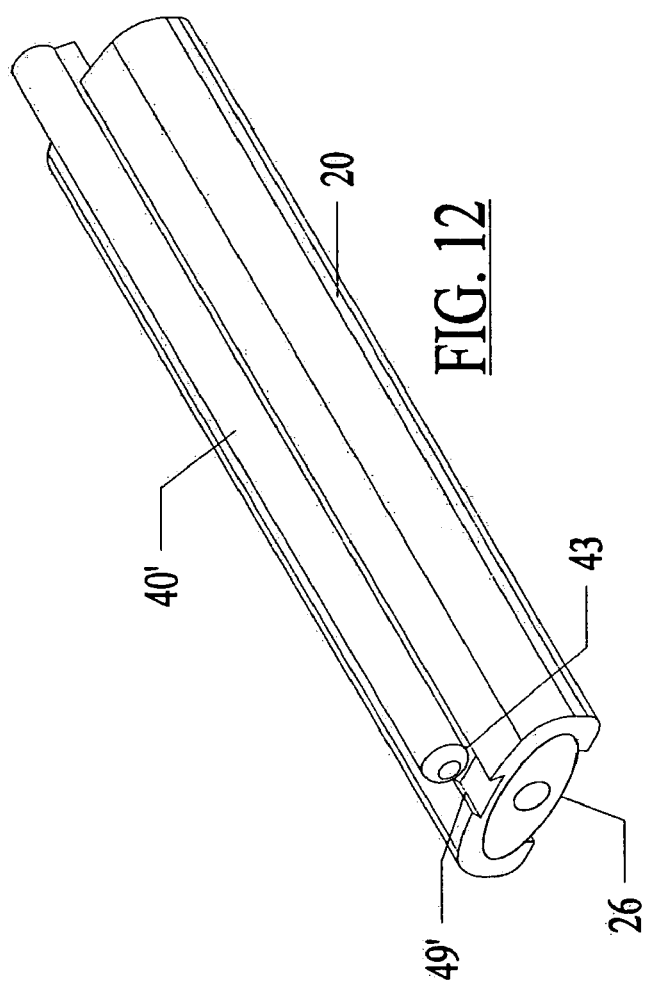
FIG. 12 is a top, side and front perspective view of a still further alternative embodiment of the tool of FIG. 2.
Figure 13:
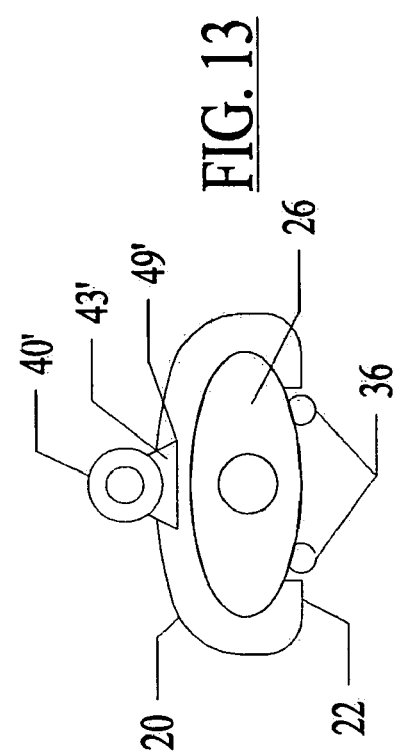
FIG. 13 is a front elevation view of the tool of FIG. 12.

During placement of the guide member 20 it would be desirable to visualize placement. FIGS. 3 and 4, an upper surface 25 of the guide member 20 carries an endoscope 40 to permit visualization of the placement of the guide member 20. FIGS. 12 and 13 illustrate an alternative embodiment with an endoscope 40' carried on a rail 43' received within a groove 49' on the upper surface 25. In this embodiment, the endoscope may be slidably moved along the length of the guide member 20. In FIGS. 12 and 13, the vacuum plenums, liners and suction holes are not shown for ease of illustration.

Enhanced Guide Member Flexibility

FIGS. 10 and 11 show an alternative embodiment for a guide member 20' with enhanced flexibility. In FIGS. 10 and 11, all elements in common with the first described embodiment are similarly numbered with the addition of an apostrophe to distinguish embodiments.

The guide member 20' is shown as formed from as a plurality of connected segmented portions 23'. The vacuum plenums 42', 42a' extend through the interconnected segments 23'. The segmentation provides for enhanced flexibility in lateral shape change of the guide member 20'. The guide member 20' (as well as guide member 20) is highly flexible and may be formed of any suitable, bio-compatible flexible material such as silicone. FIGS. 10 and 11 show reinforcing splines 23a' to maintain shape of the segments 23'.

FIGS. 10 and 11 also show an optional change in the shape of the channel 24' and carriage 26'. Sides of the channel 24' have grooves 24a' which receive rails 26a' of the carriage 26' in sliding engagement. In this embodiment, sensing electrodes (such as electrodes 36 in FIG. 3) are not shown but could be provided.

Steering or Shaping the Guide Member

FIGS. 8 and 9 illustrate one of several alternative techniques to steer and maintain the positioning of the guide member 20 when forming the desired pattern on the heart. As with the description of FIGS. 12 and 13, vacuum chambers are not shown in FIGS. 8 and 9 for ease of illustration. FIG. 8 does not show the carriage or fiber for ease of illustration. Also, an optional endoscope is not shown.

In the embodiment of FIGS. 8 and 9, an upper channel 51 (which may contain an endoscope) has a plurality of pull wires 50 contained within lumens 53. Then distal ends of the wires 50 may be anchored to a desired location on the guide member 20. Four wires 50 permit shaping the guide member in four directions (i.e., left, right, up and down).

By applying tension to selected ones of the pull wires 50, the anchored location may be moved and, as a result, the shape of the member 20 may be adjusted. The pull wires 50 permit remote steering of the distal end of the guide member 20. Also, after the position of the guide member distal end is secured on the heart, similar pull wires can be used to adjust the shape of intermediate portions of the guide member 20 as previously described.

Figure 18:
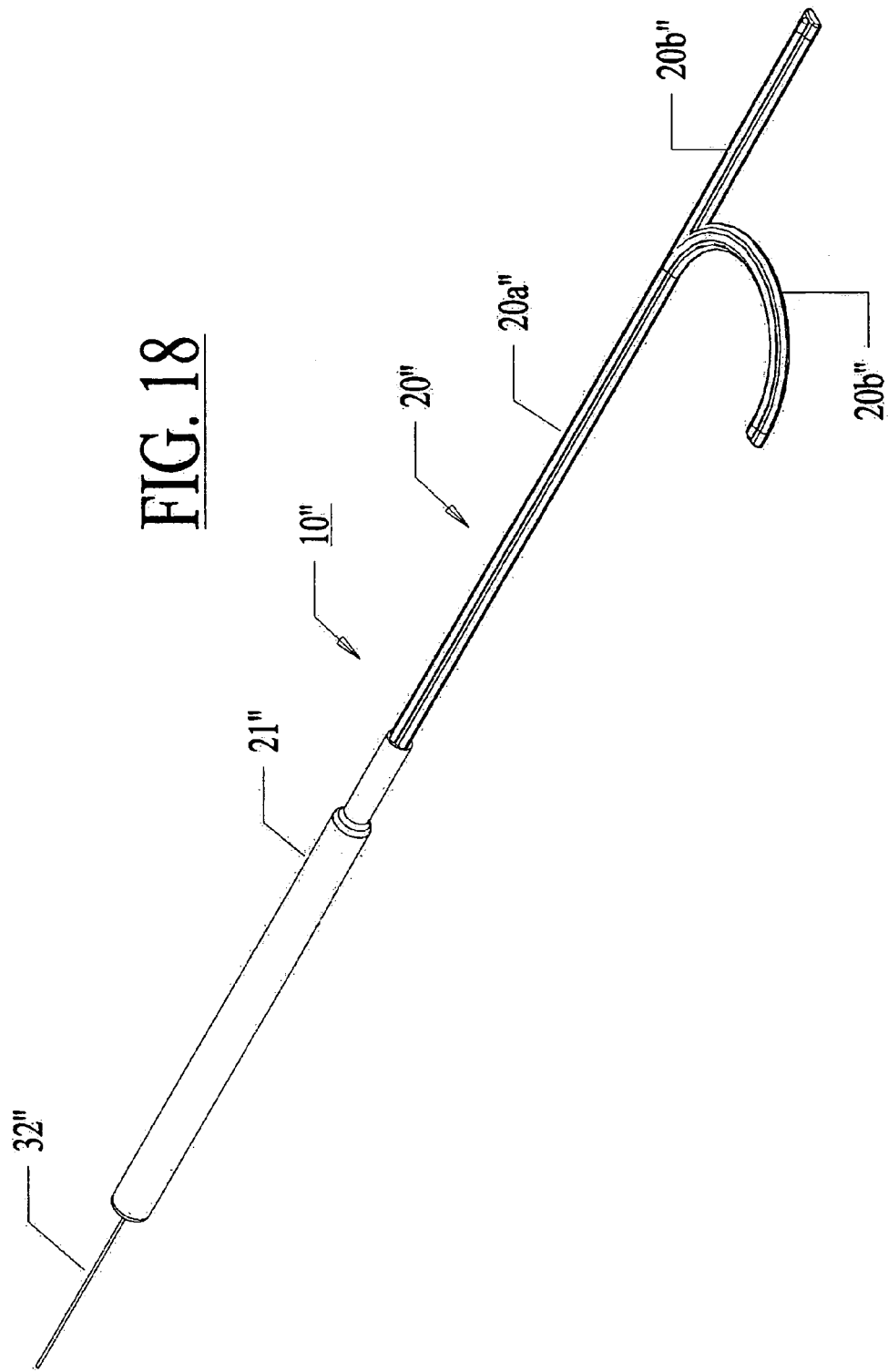
FIG. 18 is a front, left side, top perspective view of an alternative guiding system.

FIG. 18 illustrates a further embodiment which would not include steering mechanisms as previously described. Instead, the guide member 20" (which includes a channel 30" containing a carriage and fiber as described with previous embodiments) is formed of a rigid proximal portion 20a" secured to a handle 21' and a malleable distal portion 20b".

With the embodiment of FIG. 18, a surgeon could simply shape the malleable distal portion 20b" into a desired shape and place the semi-rigid shaft and malleable end through an incision formed in the patient (such as through an intercostal incision). The distal portion 20b" is then placed on the heart of the patient in the desired location for the formation of a MAZE pattern. FIG. 18 shows a distal portion 20b" in a straight configuration as well as a curved configuration to the side.

The handle and semi-rigid portion 20a" permits the surgeon to provide torque and lift to device 10" using natural leverage of the device 10" on the heart to ensure placement of the malleable distal end 20b" urged against the epicardial tissue of the heart. When the surgeon is satisfied as to the positioning, the ablation fiber can be dragged through the distal portion 20b" as previously described with the fiber carried within a carriage contained within the guide member. If desired, the guide member 20" can be provided with a plenum and holes (such as plenums 42, 42a and holes 46, 46a as described with reference to FIG. 3). Such plenums and holes would provide a vacuum assist to stabilize the distal portion 20b" against a heart surface.

Figure 19:
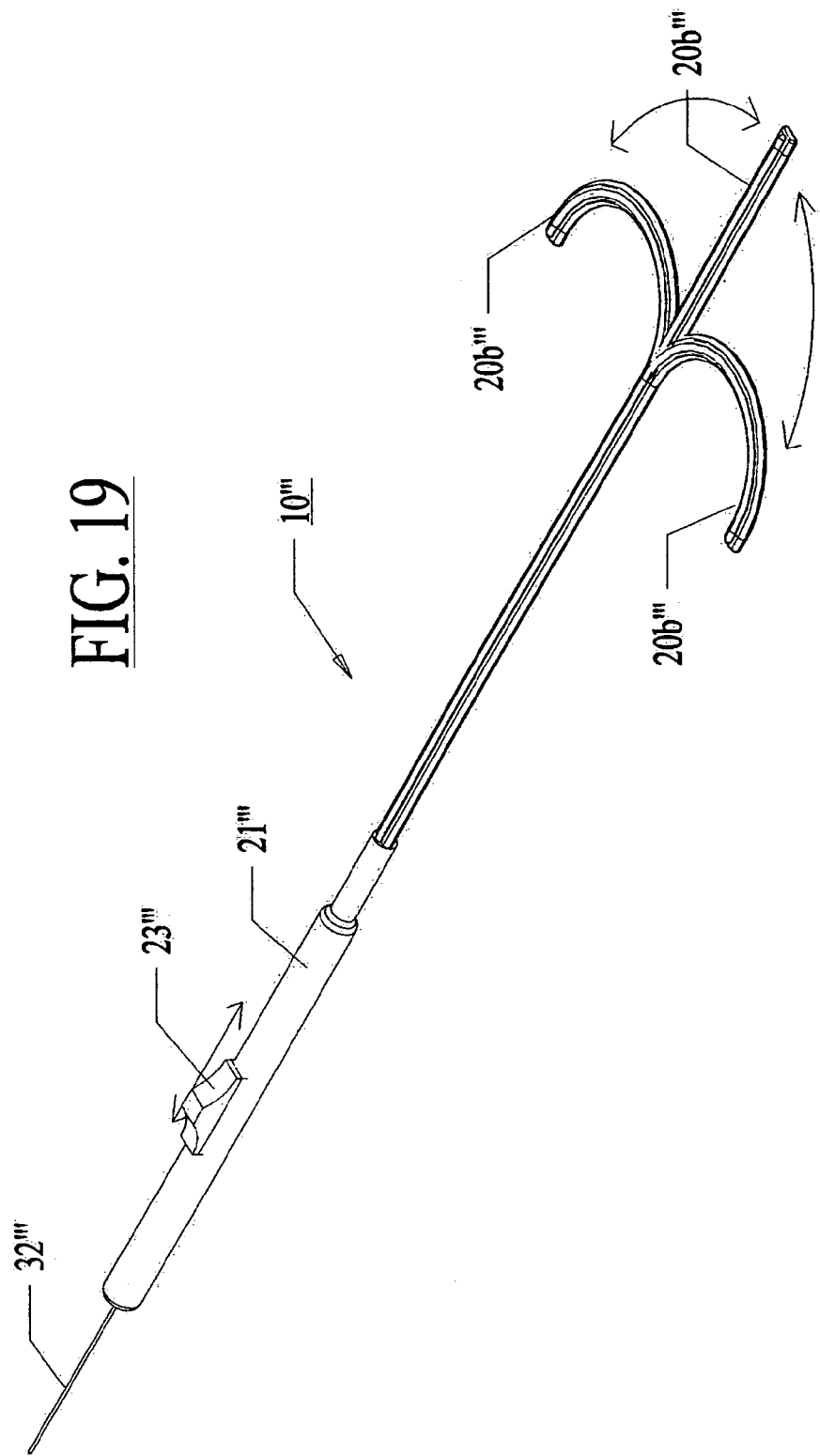
FIG. 19 is a view similar to FIG. 18 showing an alternative guiding system.

FIG. 19 shows a further alternative embodiment where the distal portion 20b''' is not malleable but is a steerable member which can bend to the right or left at the selection of an operator. The distal portion 20b''' may be coupled to a steering knob 23" by steering wires as previously described with reference to FIGS. 8 and 9. The knob 23''' on the handle 21''' provides tension to the wires and permits turning of the steerable distal portion 20b''' to either the right or left in a radius. FIG. 19 shows a distal portion 20b" in a straight configuration as well as a curved configuration to the left and right sides.

Figure 20:
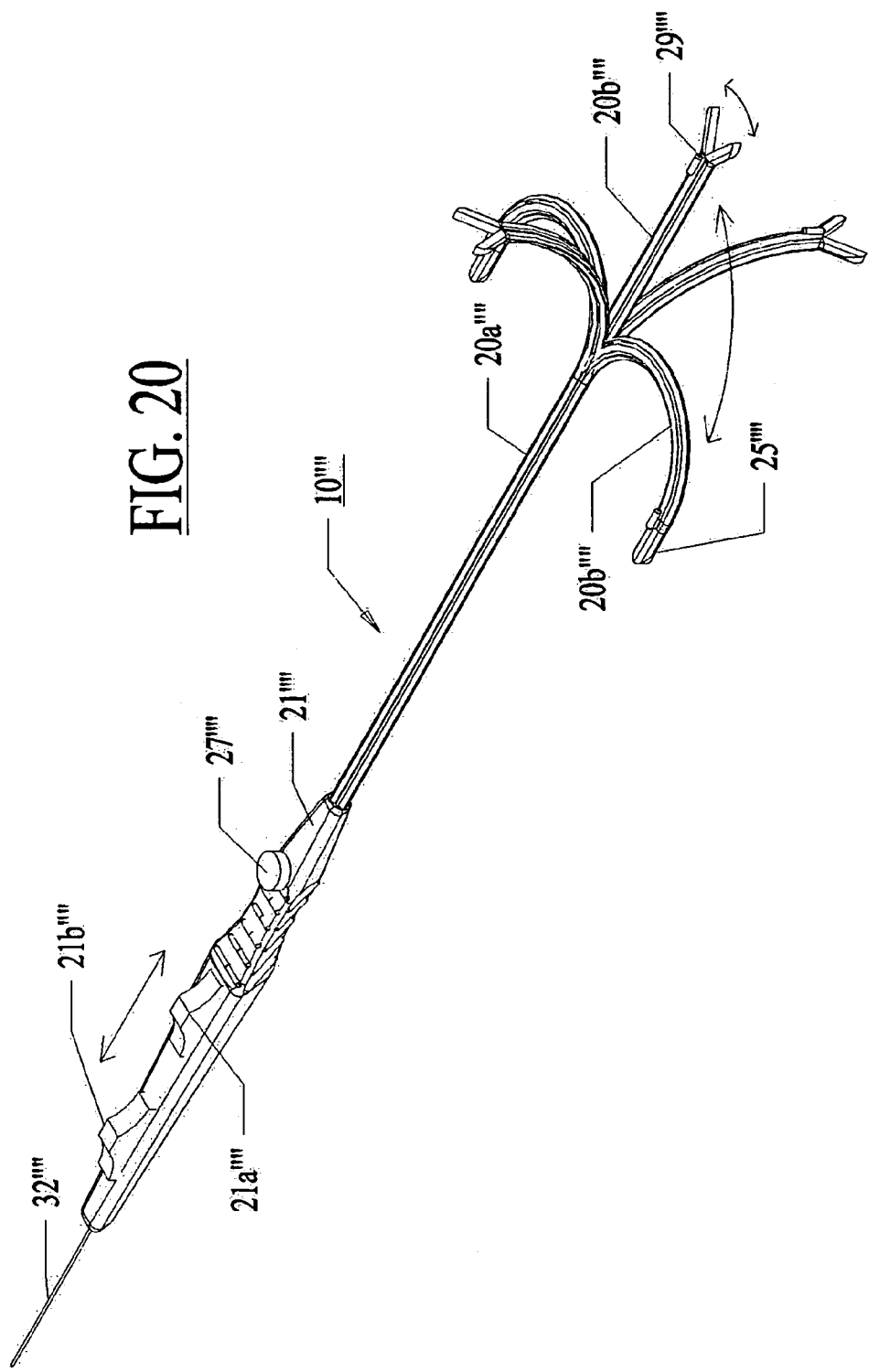
FIG. 20 is a view similar to FIG. 19 showing a further alternative guiding system.

FIG. 20 shows a still further embodiment where two steering knobs 21a"" and 21b"" are provided for steering in two planes. Further, an additional optional feature is shown where the distal tip 20a"" of the guide member 20"" is provided with a blunt dissection tool 25''''. The tool 25'''' could be either in a permanent fully closed state (not shown but would be a wedge for blunt dissection) or be selectively opened and closed jaws as illustrated in FIG. 20. The tool 25'''' is manipulated by a jaw control knob 27'''' on the handle 21''''. Also shown as an optional feature, the distal tip can be provided with an endoscopic camera 29'''' to permit visualization during use. FIG. 20 shows a distal portion 20b''' in a straight configuration as well as a curved configuration to the left and right sides and a curved position up or down.

Multi-Fiber Embodiment

In a most preferred embodiment, the optical fiber 32 with the fluid conduit 30 is pushed and pulled with the fiber's longitudinal axis generally aligned with the axis X-X of the control guide member. The fiber 32 is side-firing fiber as illustrated in FIG. 7. Light is emitted from the fiber perpendicular to the axis of the fiber 32 at the fiber tip 33. The fiber is not bent or radiused.

Figure 21:
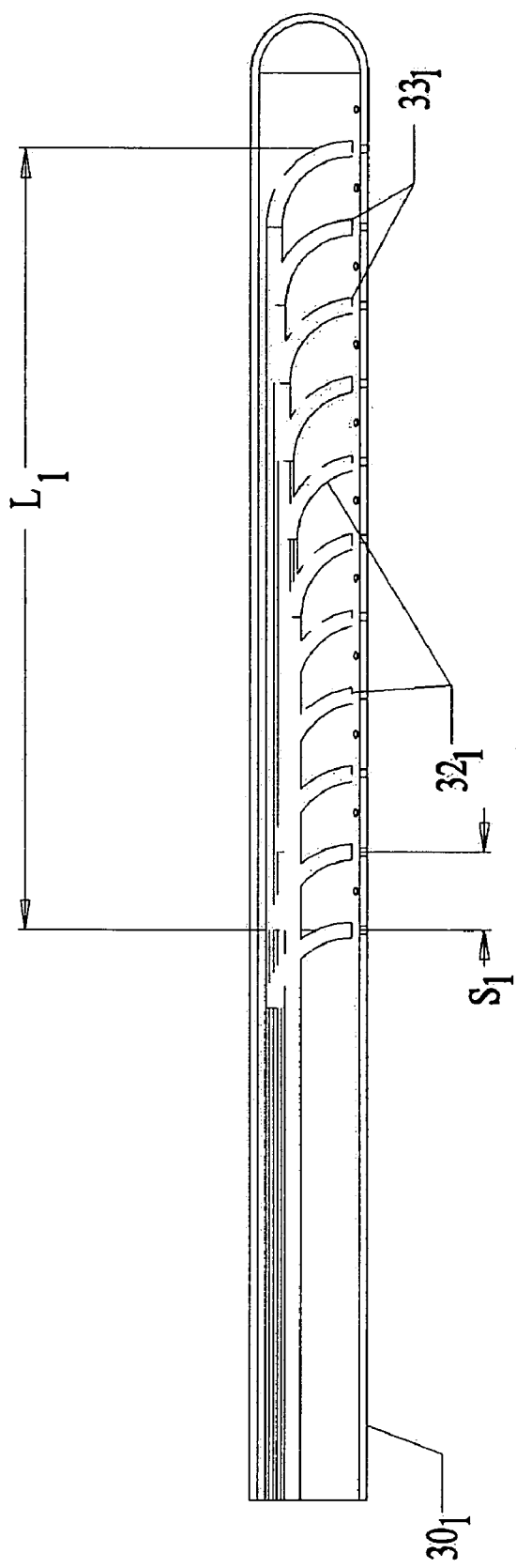
FIG. 21 is a side sectional view of a multiple fiber ablation tool.

FIG. 21 illustrates an alternative to a side-firing fiber 32. In FIG. 21, multiple fibers $32_1$ can be placed within a common channel $30_1$ which can be linearly drawn through the guide member 20.

With use of very small fibers $32_1$ (50-micron fibers), the individual fibers $32_1$ can be bent such that the fibers $32_1$ are not side firing. Instead, the fibers $32_1$ emit light out of a distal tip $33_1$ in a direction parallel to the fiber axis at the distal tip $33_1$.

The channel $30_1$ is microporous plastic transparent to the therapeutic wavelength. Micro pores $35_1$ opposing the tissue being treated permit the cooling fluid to be discharged from the channel $30_1$. The individual fibers $32_1$ are radiused to project light out of the channel $30_1$ in a generally perpendicular direction to the axis of the channel $30_1$. The ends $33_1$ of the fibers $32_1$ are spaced such that, taking into account the divergence of the emitting light, a complete transmural lesion if formed between adjacent fibers $32_1$. An appropriate spacing $S_1$ is about 2 mm. With the example given using 50-micron fibers $32_1$, the combined discharge length $L_1$ of the fiber tips $33_1$ is approximately 2 centimeters.

In this embodiment, the device is held stationary and a 2-centimeter lesion is formed. The channel $30_1$ is then slid axially within the guide member 20 a distance of 2 centimeters and held stationary for an additional application of laser energy. This process can continue in sequence until the desired pattern is completely formed.

Lesion Formation in Proximity of Coronary Vessels

In performing a MAZE procedure, difficulties are commonly encountered in forming a lesion from the epicardial surface and across a coronary vessel such as the coronary sinus or the left circumflex artery. These blood vessels lie on or near the epicardial surface. When forming a lesion through application of energy, concern exists that injury may occur to these blood vessels. This can occur by reason of application of laser energy, radio frequency energy or ultrasound energy.

One way to avoid the problem is to by-pass formation of a lesion from the epicardial surface in the region of the circumflex or coronary sinus. In this region, access is made to the interior chamber of the heart and the lesion is formed from the endocardial surface and the lesion is formed from the endocardial surface toward the epicardial surface. However, it is desirable to avoid complications associated with left atrial access. These complications could include formation of thrombus which can result in stroke or other serious adverse consequences.

Figure 22:
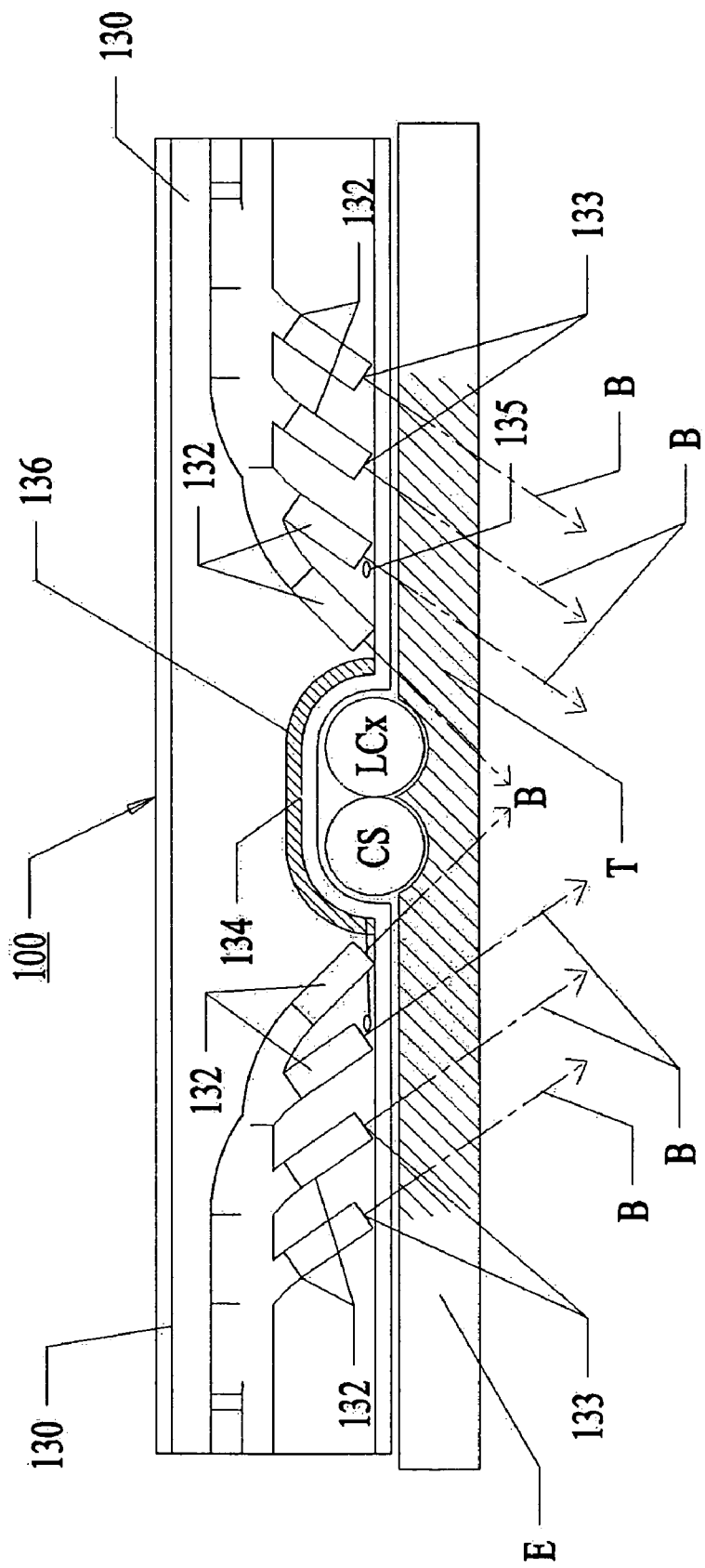
FIG. 22 is a side sectional view of an ablation tool for forming an ablation at a coronary vessel.

FIG. 22 illustrates a specific tool tip 100 for formation of a lesion along the area of the coronary sinus CS and left circumflex artery LCx shown superficial on the epicardial surface E. Fibers 132 are carried in a fluid conduit 130. The conduit 130 has a recessed portion 134 sized to be placed over the coronary sinus CS and left circumflex LCx. The fibers are placed with discharge tips 133 on opposite sides of the recess 134. Fluid discharge holes 135 are positioned to pass a cooling fluid from the conduit 130 to the epicardial surface E.

A reflective coating 136 is formed on the recessed portion 136 to form a reflective surface. The reflective coating 136 is selected to reflect the therapeutic wavelength of the laser energy being emitted from fiber tips 133.

Fibers 132 are arranged on opposite sides of the recessed portion 134 with the fiber tips 133 directed to form an angled discharge of light in a pattern illustrated by arrows B. The light paths B converge beneath the coronary sinus CS and left circumflex LCx to create a lesioned tissue T in the epicardium surface E beneath the coronary sinus and left circumflex and originating on opposite sides of the vessels CS, LCx. Accordingly, a lesion is formed through the atrial tissue but without application of laser energy directly to the left circumflex LCx or coronary sinus CS. The surface of the recessed portion 134 may be additionally cooled by applying either cryogenics to the recessed portion 134 or with an electronic cooling member (such as a Peltier cooling element) on the recessed portion 134.

As an alternative to the above, the left circumflex LCx and coronary sinus CS can be dynamically cooled during the laser treatment. Dynamic cooling is described in U.S. Pat. Nos. 6,514,244 and 6,200,308 (both incorporated herein by reference). In applying the concept of dynamic cooling to laser energy ablation of cardiac tissue surrounding and beneath the left circumflex or coronary sinus, a cryogenic energy pulse is alternated and/or applied simultaneously to laser energy application. Since epicardial application of cryogenic fluid or gas would cool the outer most layers of cardiac tissue, this would serve to protect the left circumflex and coronary sinus from temperature elevation above 55 degrees C., as theses structures are typically closer to the epicardial rather than the endocardial surface. This induced temperature gradient would allow direct laser application over the left circumflex coronary artery and coronary sinus, and negate the need to know the exact anatomic location of these structures prior to laser ablation.

Pulmonary Vein Isolation

Figure 24:
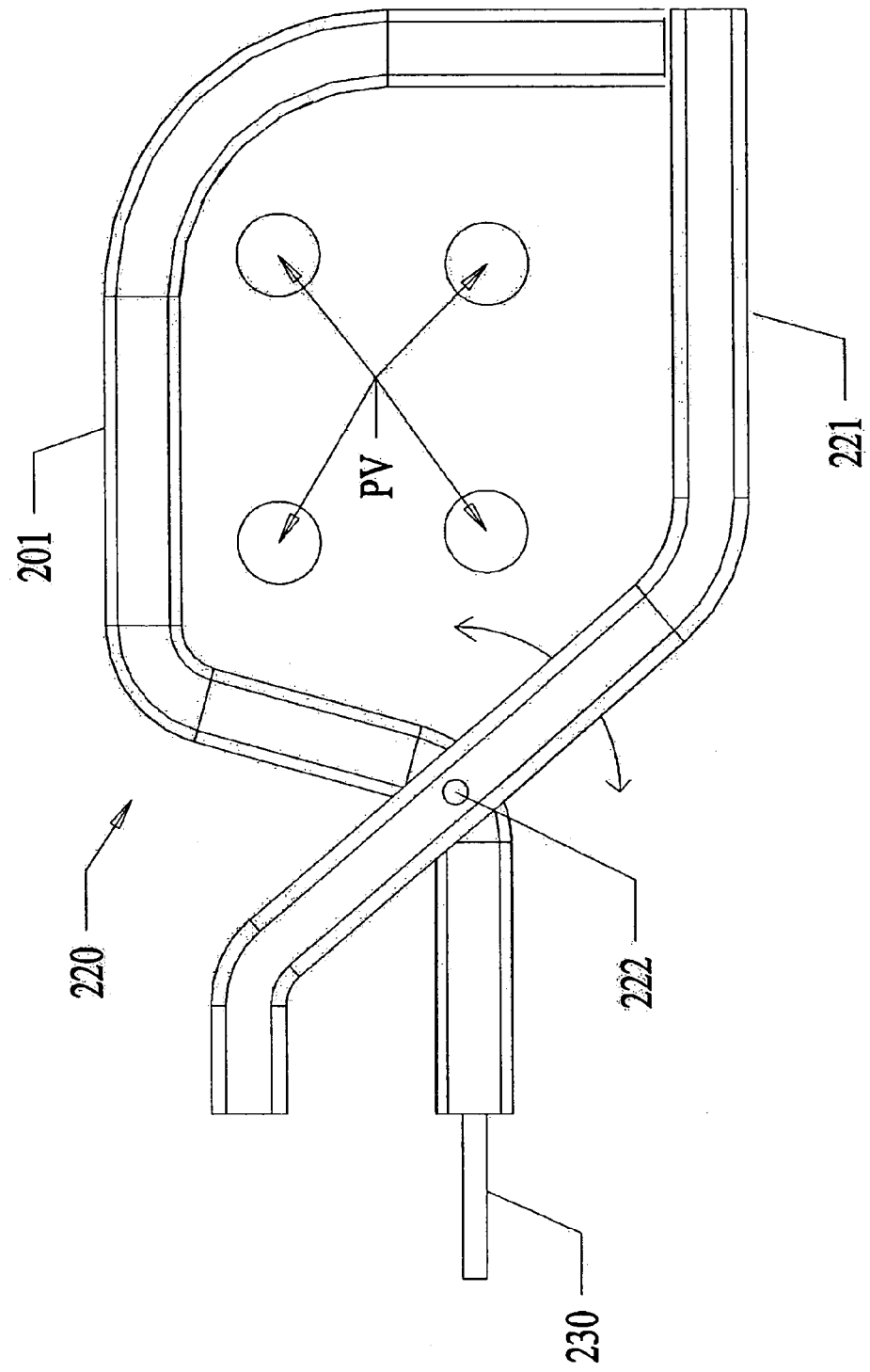
FIG. 24 is a top plan view of a guide member surrounding pulmonary veins.

In a MAZE procedure it is known to be desirable to electrically isolate the pulmonary veins by forming a MAZE lesion around the veins. FIG. 24 illustrates an embodiment of a composite guide member 220 for this purpose. The composite guide member 220 includes a first guide member 220a pivotally connected to a second guide member 220b at a pivot point 222. Each contains a carriage and fiber as described with respect to guide member 20 and, preferably, contain vacuum or other apparatus as previously described to urge the bottom surfaces of the guide members 220a, 220b against the heart surface.

The first guide member 220a is pre-shaped to at least partially surround the pulmonary veins PV. The second guide member 220b completes a perimeter around the pulmonary veins PV. So positioned, the conduit 230 (containing the optical fiber as previously described) is moved through the first guide member 220a while energizing the fiber to form a MAZE pattern partially surround the veins PV. Similarly, a carriage and fiber are moved through the second guide member 220b to complete the encirclement of the pulmonary veins PV.

It has been shown how the objects of the invention have been achieved in a preferred embodiment. It is intended that such modifications and equivalents which will appear to one of ordinary skill in the art with the benefit of the teachings of the present invention shall be included within the scope of the claims.

What is claimed:

1. A method for assessing efficacy of a lesion formed on a human heart where said lesion is intended to be formed as a transmural lesion through a wall thickness of myocardial tissue and with said lesion having a depth dimension of penetration into said tissue, an elongated dimension on a surface of said tissue and a narrow width dimension transverse to said elongated dimension, said method comprising:
   (a) placing a first electrode at said tissue on a first side of said lesion;
   (b) placing a second electrode at a said tissue on a second side of said lesion with said lesion between said first and second sides;
   (c) applying an electrical signal to said first electrode;
   (d) noting a received response to said electrical signal at said second electrode; and
   (e) processing said received response to both determine (i) an existence of a discontinuity of said lesion and (ii) approximating a position of a location of said discontinuity along said elongated dimension.

2. A method according to claim 1 wherein said received response is a time delay between an application of said electrical signal to said first electrode and a receipt of said response at said second electrode.

3. A method according to claim 1 wherein said received response is a measure of conductance between said first electrode and said second electrode.

4. A method according to claim 1 wherein said received response is an alteration of a waveform of said electrical signal between said first electrode and said second electrode.

5. A method according to claim 1 wherein said lesion is formed as an intended complete lesion surrounding a pulmonary vein and defining a bounded area within said lesion, said method further comprising:
   (a) placing multiple pairs of said first and second electrodes on said first and second sides;
   (b) applying separate ones of said electrical signal to said first electrodes of said pairs;
   (c) noting separate ones of said received response to said separate ones of said electrical signal at said second electrodes; and
   (d) comparing said separate ones of said received response to approximate a location of a discontinuity of said lesion based on said received response.

6. A method according to claim 5 wherein said received response is a time delay between an application of said electrical signal to said first electrode and a receipt of said response at said second electrode.

7. A method according to claim 5 wherein said received response is a measure of conductance between said first electrode and said second electrode.

8. A method according to claim 5 wherein said received response is an alteration of a waveform of said electrical signal between said first electrode and said second electrode.

9. A method for forming a lesion in a heart tissue, said method comprising:
   (a) forming at least a segment of a lesion on a human heart where said lesion is intended to be formed as a transmural lesion through a wall thickness of myocardial tissue and with said lesion having a depth dimension of penetration into said tissue, an elongated dimension on a surface of said tissue and a narrow width dimension transverse to said elongated dimension;
   (b) assessing a rransmurality of said lesion by:
      (ii) placing a first electrode at said tissue on a first side of said lesion;
      (ii) placing a second electrode at a said tissue on a second side of said lesion with said lesion between said first and second sides;
      (iii) applying an electrical signal to said first electrode;
      (iv) noting a received response to said electrical signal at said second electrode;
      (v) processing said received response to both determine
         (i) an existence of a discontinuity of said lesion and
         (ii) approximating a position of a location of said discontinuity along said elongated dimension and
   (c) repeating a formation of said lesion at said location.

10. An apparatus for forming a lesion in tissue along a desired ablation path, said apparatus comprising:
   a guide member having a tissue-opposing surface for placement against a heart surface;
   an ablation member having an ablation element for directing ablation energy in an emitting direction;
   said ablation member coupled to said guide member to move in a longitudinal path relative to said guide member and with said ablation member oriented relative to said guide member for said emitting direction to be directed away from said tissue opposing surface;
   a transmurality assessor for assessing efficacy of a lesion formed by said ablation member wherein said transmurality assessor includes:
   (a) a first electrode for placement at said tissue on a first side of said lesion;
   (b) a second electrode for placement at a said tissue on a second side of said lesion with said lesion between said first and second sides;
   (c) said electrodes adapted for connection to a source of an electrical signal for applying said electrical signal to said first electrode;
   (d) said electrodes adapted for connection to a monitoring equipment for processing a received response to both determine (i) an existence of a discontinuity of said lesion and (ii) approximating a position of a location of said discontinuity along
   said elongated dimension.

11. An apparatus according to claim 10 wherein said electrodes are attached to said guide member.

12. An apparatus according to claim 11 wherein said electrodes are attached to said ablation member for movement therewith.

* * * * *

UNITED STATES PATENT AND TRADEMARK OFFICE
CERTIFICATE OF CORRECTION

PATENT NO.       : 7,232,437 B2                                              Page 1 of 1
APPLICATION NO.  : 11/133900
DATED            : June 19, 2007
INVENTOR(S)      : Berman et al.

It is certified that error appears in the above-identified patent and that said Letters Patent is hereby corrected as shown below:

Title page, (56) references cited, U.S. Patent Documents: insert the following omitted U.S. Patents in appropriate order:

--5,931,848         08//1999      Saadat
2002/0193782 A1     12//2002      Ellis et al.
2003/0078566 A1     04/2003       Elliott et al.
2003/0109868 A1     06/2003       Chin et al.--

Col. 12, line 54: "Transmurality of Lession" should read --Transmurality of Lesion--

Col. 22, line 10, claim 9: "accessing a rransmurality of said" should read --accessing a transmurality of said--

Signed and Sealed this

Twenty-seventh Day of November, 2007

JON W. DUDAS
*Director of the United States Patent and Trademark Office*